(12) United States Patent
Edrich et al.

(10) Patent No.: US 8,296,071 B2
(45) Date of Patent: Oct. 23, 2012

(54) METHODS FOR UNIFORMLY TREATING BIOLOGICAL SAMPLES WITH ELECTROMAGNETIC RADIATION

(75) Inventors: Richard Alan Edrich, Denver, CO (US); Laura Goodrich, Lakewood, CO (US); Glen Delbert Antwiler, Lakewood, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 1892 days.

(21) Appl. No.: 11/079,894

(22) Filed: Mar. 14, 2005

(65) Prior Publication Data

US 2005/0202395 A1 Sep. 15, 2005

Related U.S. Application Data

(60) Provisional application No. 60/553,686, filed on Mar. 15, 2004.

(51) Int. Cl.
*G01N 33/48* (2006.01)
(52) U.S. Cl. .......................................... 702/19
(58) Field of Classification Search .................. None
See application file for complete search history.

(56) References Cited

U.S. PATENT DOCUMENTS

| | | | |
|---|---|---|---|
| 4,769,131 A * | 9/1988 | Noll et al. ............... 210/85 |
| 4,915,683 A | 4/1990 | Sieber | |
| 5,516,629 A | 5/1996 | Park et al. | |
| 5,545,516 A | 8/1996 | Wagner | |
| 5,587,490 A | 12/1996 | Goodrich et al. | |
| 5,607,924 A | 3/1997 | Magda et al. | |
| 5,627,308 A * | 5/1997 | Dahneke ............. 73/28.01 |
| 6,219,584 B1 * | 4/2001 | Lee ..................... 700/90 |
| 6,268,120 B1 | 7/2001 | Platz et al. | |
| 6,277,337 B1 | 8/2001 | Goodrich, Jr. et al. | |
| 6,464,936 B1 | 10/2002 | Mowat et al. | |
| 6,565,802 B1 | 5/2003 | Hanley et al. | |
| 6,586,172 B1 | 7/2003 | Gunn et al. | |
| 2002/0177118 A1 | 11/2002 | Coogan et al. | |
| 2003/0035751 A1 | 2/2003 | Hanley et al. | |
| 2003/0049809 A1 | 3/2003 | Kaiser et al. | |
| 2003/0138346 A1 | 7/2003 | Gunn et al. | |
| 2003/0165398 A1 | 9/2003 | Waldo et al. | |
| 2004/0021089 A1 | 2/2004 | Cimino et al. | |

FOREIGN PATENT DOCUMENTS

| | | |
|---|---|---|
| WO | WO 00/20045 | 4/2000 |
| WO | WO 01/54738 | 8/2001 |
| WO | WO 01/60418 * | 8/2001 |
| WO | WO 01/74407 | 10/2001 |
| WO | WO 01/96340 | 12/2001 |
| WO | WO 02/26270 | 4/2002 |
| WO | WO 02/26270 A3 | 4/2002 |
| WO | WO 02/38191 | 5/2002 |
| WO | WO 2004/032782 | 4/2004 |
| WO | WO 2004/033081 | 4/2004 |
| WO | WO 2004/075931 | 9/2004 |

OTHER PUBLICATIONS

International Search Report for PCT/US2005/008690, mailed Jun. 3, 2005.
European Search Report, Corresponding to European Application No. 08006164.1-2113, dated Jul. 15, 2008.

* cited by examiner

*Primary Examiner* — Pablo Whaley
(74) *Attorney, Agent, or Firm* — John R. Merkling; Edna M. O'Connor

(57) ABSTRACT

Methods, devices and device components are presented for uniformly treating fluids undergoing mixing with electromagnetic radiation. In one aspect, the present invention provides methods of treating a fluid undergoing continuous fluid mixing wherein net radiant energies necessary to provide uniform treatment of the fluid samples with electromagnetic radiation are calculate on the basis of the volume, mass or mixing rate of the fluid or any combination of these variables. In another aspect, the present invention provides algorithms for determining net radiation energies, radiant powers, and/or illumination times necessary for providing uniform treatment of fluid samples. The present invention provides methods for uniformly reducing pathogens in biological fluids, including blood and blood components.

41 Claims, 7 Drawing Sheets

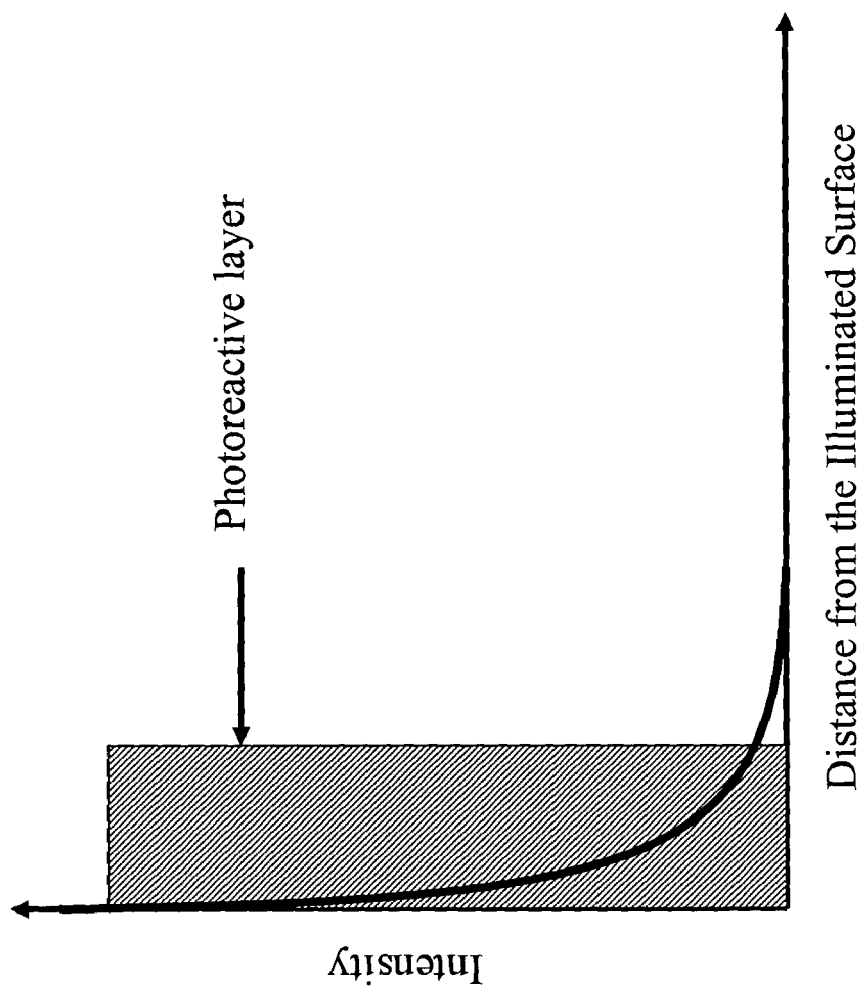

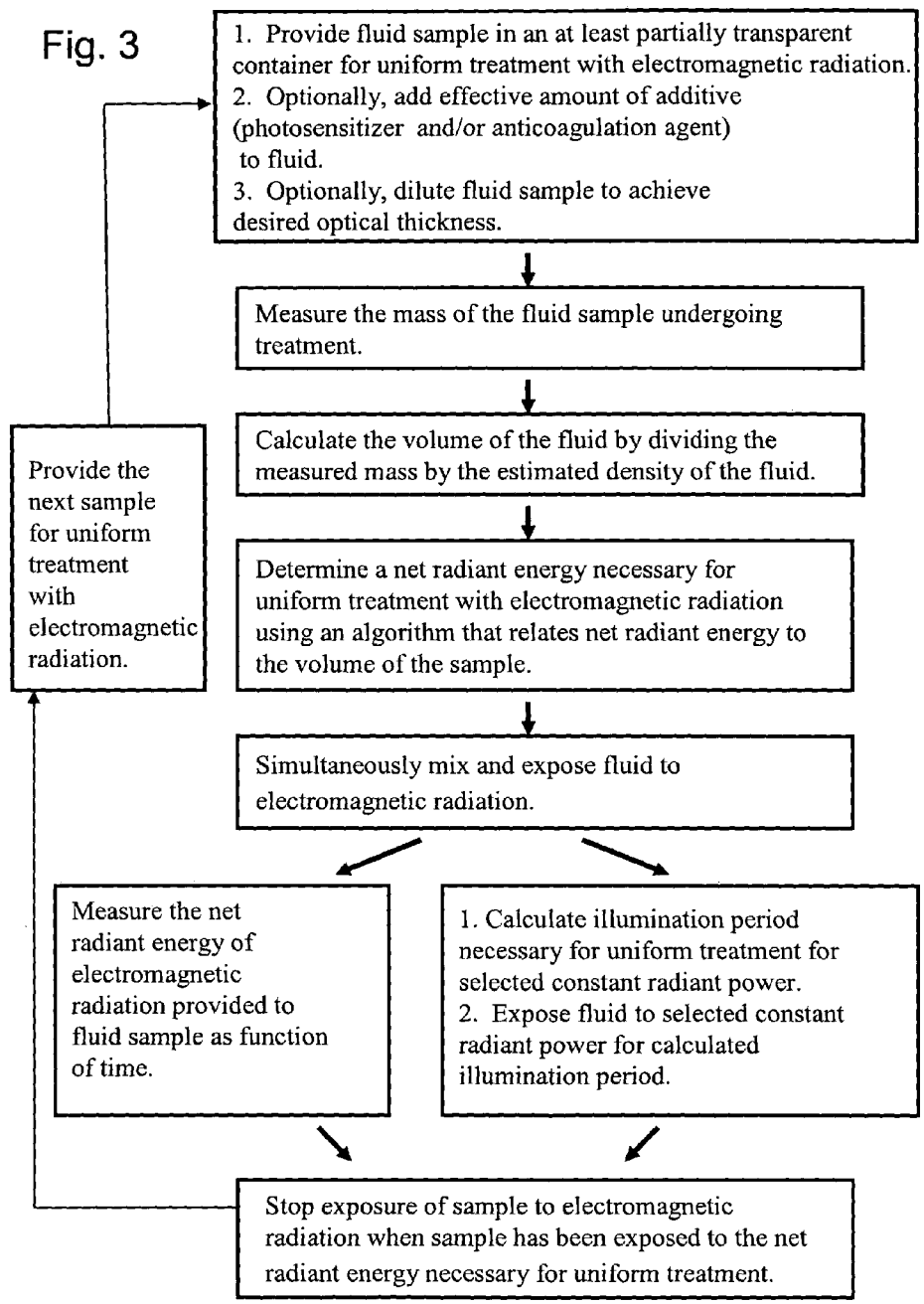

METHODS FOR UNIFORMLY TREATING BIOLOGICAL SAMPLES WITH ELECTROMAGNETIC RADIATION

CROSS-REFERENCE TO RELATED APPLICATIONS

This application claims priority under 35 U.S.C. 119(e) to U.S. provisional Patent Application No. 60/553,686 filed Mar. 15, 2004, which is hereby incorporated by reference in its entirety to the extent not inconsistent with the disclosure herein.

BACKGROUND OF THE INVENTION

Collection, processing and purification of biological samples are important processes in a range of medical therapies and procedures. Important biological samples used as therapeutic and/or re-infusion agents include whole blood and purified blood components, such as red blood cells, platelets, white blood cells and plasma. In the field of transfusion medicine, one or more whole blood components are directly introduced into a patient's blood stream to replace a depleted or deficient component. Infusion of plasma-derived materials, such as blood proteins, also plays a critical role in a number of re-infusion processes and other important therapies. For example, plasma-derived immunoglobulin is commonly provided to supplement a patient's compromised immune system. Due to increases in the demand for purified biological samples for transfusion, infusion and transplantation therapies, substantial research efforts have been directed at improving the availability, safety and purity of biological samples used as therapeutic and/or re-infusion agents.

While biological samples used for re-infusion or other purposes are currently safer than in the past, the risk of exposure to pathogens in human blood samples remains significant. A large number of deleterious contaminants have been identified in intracellular and extracellular fractions of human blood. For example, it is estimated that approximately 1 in 34,000 donated blood and blood component samples are contaminated with viral contaminants such as human immunodeficiency virus type I/II (HIV), hepatitis B and C (HVB and HVC) or human T-lymphotropic virus type I/II (HTLV I/II). Bacterial contaminants are even more common than viral contaminants in donated blood and blood component samples and may reach an incidence of contamination as high as about 1 in 2000 samples. Contamination of donated blood components with donor leukocytes is another frequently encountered problem.

In addition to these known risks, it has also been demonstrated that human blood reservoirs are routinely contaminated with other pathogens which are not assayed in conventional blood screening protocols, including transfusion-transmitted virus, hepatitis G virus, human herpes virus 8, HTLV-2, hepatitis A, TT virus, SEN-V malaria, babesia, trypanosome, and parvo B19 virus.

Over the last decade, a number of methods have been developed for reducing the risks associated with pathogenic contaminants in biological samples, especially donated blood components. One promising approach to reducing risks associated with contamination of these materials is to use chemical or physical pathways to reduce the biological activities of pathogens present in biological samples or render them incapable of replication. Over the last decade, a variety of methods for reducing the biological activities of pathogens in biological fluids have been developed, including, direct photoreduction, use of detergents for inactivating viruses having lipid membranes, chemical treatment methods and photoinduced chemical reduction techniques. Due to their compatibility with high-volume pathogen inactivation, efficiency and demonstrated efficacy, photoinduced chemical reduction and direct photoreduction have emerged as two especially promising techniques for treating biological samples. U.S. Pat. Nos. 6,277,337, 5,607,924, 5,545,516, 4,915,683, 5,516,629, and 5,587,490 describe exemplary applications of photoinduced chemical reduction methods and direct photoreduction methods for reducing of pathogens in blood.

In photoinduced chemical reduction methods, effective amounts of one or more photosensitizers are added to a biological fluid, which may be subsequently mixed and illuminated with electromagnetic radiation. Illumination activates the photosensitizers, thereby initiating chemical reactions and/or physical processes which kill the pathogens present in the sample or substantially prevent pathogens from replicating. In direct photoreduction methods, illumination with electromagnetic radiation having selected wavelengths directly results in pathogen reduction.

An important consideration in photoinduced chemical reduction and direct photoreduction methods is that exposure of some blood components to electromagnetic radiation can deleteriously affect their biological activities and vitalities. Decreases in biological activities and vitalities from exposure to electromagnetic radiation may reduce the effectiveness of these materials as therapeutic and/or re-infusion agents. Therefore, a compromise often exists in photoinduced chemical reduction and direct photoreduction methods between optimizing the extent of pathogen reduction and minimizing damage to blood components comprising therapeutic and/or re-infusion agents.

Another important consideration in photoinduced chemical reduction and direct photoreduction methods is the ability of these methods to provide uniform treatment for fluid samples having characteristics that are commonly subject to variation, such as the volumes, masses, donor identities and the concentrations of cellular and non-cellular components of samples. For example, conventional pathogen reduction procedures that deliver the same net radiant energy per illuminated area to all treated blood and blood component samples may result in nonuniform treatment that varies systematically with the volume of the blood or blood product samples undergoing treatment. As blood and blood components typically exhibit a range of sample volumes depending on the physical attributes of the donor and the procedures employed for collection and processing, this practical limitation may result in blood products having pathogen concentrations and therapeutic qualities that vary significantly. Such undesirable variations can significantly undermine quality control efforts and may negatively impact product validation and regulatory approval.

It will be appreciated from the foregoing that a clear need exists for methods and devices for uniformly treating biological fluids with electromagnetic radiation. Specifically, methods and devices are needed that provide equivalent treatment of fluid samples with electromagnetic radiation, regardless of properties of the samples subject to variation such as the volumes or masses of the samples. In addition, methods and devices for treating fluid samples with electromagnetic radiation are needed that generate treated samples having comparable levels of pathogens and having components comprising therapeutic and/or re-infusion agents exhibiting comparable biological activities and viabilities.

SUMMARY OF THE INVENTION

This invention provides methods, devices and device components for uniformly treating fluids undergoing mixing with electromagnetic radiation, particularly useful for treating fluids comprising materials that efficiently scatter and/or absorb incident electromagnetic radiation. Methods of the present invention are capable of uniformly treating fluid samples with electromagnetic radiation, regardless of physical characteristics of the samples that are commonly subject to variation, such as the volumes and masses of treated fluid samples. The present invention provides a reproducible means of uniformly delivering electromagnetic radiation throughout entire volumes of fluid samples so that treated samples have compositions suitable for subsequently use in a selected application.

Uniformity in this description relates to two beneficial attributes of the present methods. First, uniformity refers to delivery of electromagnetic radiation to the entire volume of a fluid such that substantially all the particles comprising the fluid are exposed to equivalent effective net radiant energies. Second, uniformity refers to treatment of a plurality of fluid samples with electromagnetic radiation such that each fluid sample undergoes equivalent treatment, regardless of differences in their physical characteristics, such as differences in their respective volumes, masses and mixing rates during processing. In this context, equivalent treatment may refer to equivalent end results of a treatment process, such as reduction of pathogens throughout the entire volumes of different samples to comparable levels, or may refer to treatment wherein substantially all the particles of the plurality of samples are exposed to the equivalent effective net radiant energy during processing.

In one aspect of the present invention, the entire volumes of fluid samples undergoing mixing are treated with electromagnetic radiation having a net radiant energy, radiant power or both that are selected on the basis of characteristics of the sample and processing technique that determine the rate of transport of particles comprising the fluids through a photoreactive layer formed upon illumination. For example, net radiant energies and/or radiant powers in some methods of the present invention are selected on the basis of the volume, mass and/or mixing rate of the fluid sample or any combination of these variables. In another embodiment of this aspect of the invention, sample agitation rates of fluid samples undergoing simultaneous mixing and treatment with electromagnetic radiation are selected on the basis of the volumes and/or masses of the samples to ensure that particles comprising the different samples are exposed to equivalent effective net radiant energies during processing.

In another aspect, the present invention provides methods, devices and device components for uniformly reducing the biological activities of pathogens in plurality of fluid samples by treatment with electromagnetic radiation. In an exemplary method of this aspect of the present invention, fluid samples are provided in at least partially transparent containers and subjected to mixing during treatment. Net radiant energies to be delivered to each of the samples are determined on the basis of the volume, mass and/or mixing rate of individual fluid samples undergoing treatment or any combination of these variables. In an embodiment of the present methods useful for uniformly reducing pathogens in a plurality of fluid samples, net radiant energies provided to each sample are selected on the basis of the volumes, masses and/or mixing rates of the samples such that substantially all the particles of each of the fluid samples are exposed to equivalent effective net radiant energies.

During processing, electromagnetic radiation having a selected radiant power is directed onto one or more at least partially transparent surfaces of the container for a selected illumination time. In this embodiment of the present invention, radiant powers and illumination times are variables that are selected to provide the appropriate net radiant energy to each fluid sample necessary to provide uniform treatment with electromagnetic radiation. Exposure of the fluid to electromagnetic radiation occurs in a photoreactive layer located proximate to the surface of the fluid that is illuminated with electromagnetic radiation. In the photoreactive layer, electromagnetic radiation interacts with particles in the fluid, thereby inducing chemical and/or physical changes resulting in a reduction of pathogens. Mixing of the fluid in the container transports fluid through the photoreactive layer providing a means of uniformly distributing the delivered electromagnetic radiation to the entire volume, and thus reducing pathogens throughout the entire volume of the sample. Optionally, methods of this aspect of the present invention further comprise the step of adding an effective amount of one or more additives to the fluid to the fluid, such as photosensitizers, enhancers, stabilizers, anticoagulant agents, diluents, preservatives and all combinations of these. Additives may be added to the fluid undergoing processing before, during or after treatment with electromagnetic radiation.

In one embodiment of this aspect of the present invention, the fluid is exposed to electromagnetic radiation having wavelengths, intensities and/or radiant powers which directly reduce the biological activities of pathogens throughout the entire volume of the sample. Alternatively, the present invention includes methods wherein a photosensitizer is provided to the entire volume of the fluid sample undergoing processing and exposed to electromagnetic radiation having wavelengths, intensities, and/or radiant powers which initiate photochemical reactions involving the photosensitizer that reduce the biological activities of pathogens throughout the entire volume of the sample.

Optionally, the methods of the present invention may include the step of determining the volume and/or mass of fluid samples prior to treatment with selected net radiant energies. In one embodiment, the volume of a fluid sample is directly measured prior to illumination. Alternatively, the present invention includes methods wherein the volume of a fluid sample is determined by measuring the mass of the fluid sample and dividing the measured mass by the density of the fluid or an estimate thereof. Methods of the present invention may further comprise the step of generating an output signal corresponding to the measured volume or mass and transmitting this output signal to a device or device component, such as an electromagnetic radiation source controller, capable of executing an algorithm that determines net radiant energies, radiant powers and/or illumination times necessary for achieving pathogen reduction in fluid samples.

In one embodiment of this aspect of the present invention, methods of treating a fluid with electromagnetic radiation are provided wherein net radiant energies delivered to the samples are inversely correlated to the fluid mixing rates of fluid samples undergoing treatment. In this aspect of the present invention, for example, less net radiant energy is provided to fluids subjected to higher fluid mixing rates than to fluids subjected to lower fluid mixing rates. In the present invention, net radiant energies and mixing rates may be inversely related in any manner resulting in effective treatment of a fluid with electromagnetic radiation including, but not limited to, a linear or substantially linear manner, an exponential or substantially exponential manner, a logarithmic or substantially logarithmic manner, a quadratic substantially quadratic manner or any combination of these functional relationships.

In another embodiment of this aspect of the present invention, methods of treating a fluid with electromagnetic radiation are provided wherein the net radiant energies delivered to the samples are positively correlated (i.e. proportional) to the volumes or the masses of the fluid samples undergoing treatment. In the context of this application of the methods of the present invention, the term "volume of fluid" and "mass of fluid" refers to the volume and mass of fluid present in the container during illumination and includes any additives that are provided to the fluid prior to or during illumination. For example, fluids having larger volumes and/or masses are exposed to larger net radiant energies than fluids having smaller volumes and/or masses. In some embodiments, the benefits of using net radiant energies positively correlated to the volumes or the masses of the fluid samples undergoing treatment arises from mixing considerations involved with mixing fluid samples held in equivalent fixed volume containers. For fluid mixing via sample agitation techniques, for example, fluids having larger volumes tend to undergo smaller fluid mixing rates than fluids having smaller volumes held in similar fixed-volume containers. Net radiant energies and fluid volumes and/or masses in the present invention may be positively correlated in any manner resulting in effective treatment of a fluid with electromagnetic radiation including, but not limited to, a linear or substantially linear manner, an exponential or substantially exponential manner, a logarithmic or substantially logarithmic manner, a quadratic substantially quadratic manner or any combination of these functional relationships.

The ability of the present invention to uniformly treat fluids with electromagnetic radiation is particularly beneficial for use of the present methods for pathogen reduction of fluids. Pathogen reduction by uniform treatment of fluid samples with electromagnetic radiation is useful for avoiding exposure of samples having smaller volumes and/or masses to net radiant intensities larger than those required for effective pathogen reduction and/or for avoiding exposure of fluid samples having larger volumes and/or masses to net radiant intensities smaller than those required for effective pathogen reduction. Uniform treatment of samples with electromagnetic radiation provided by the present methods also ensures that entire volumes of fluid samples undergoing processing are provided sufficient radiant energies of electromagnetic radiation to achieve effective pathogen reduction for subsequent use of the treated fluid samples, for example subsequent use as therapeutic and/or re-infusion agents. Pathogen reduction methods of this aspect of the present invention, therefore, are capable of generating treated fluids having concentrations of pathogen below a well defined, predetermined level. Further, pathogen reduction by uniform treatment of fluid samples with electromagnetic radiation is useful for maintaining, and in some instances optimizing, the biological activities and vitalities of treated fluid components comprising therapeutic, re-infusion or diagnostic agents in fluid samples by avoiding overexposure of these components to intensities of electromagnetic radiation that result in loss or damage to them.

In another aspect, the present invention provides algorithms for calculating illumination parameters useful for treating fluid samples with electromagnetic radiation. Algorithms of this aspect of the present invention use measured, calculated or estimated volumes, masses and/or mixing rates of fluid samples to determine net radiant energies, radiant powers and/or illumination times necessary to provide uniform treatment of the fluid samples with electromagnetic radiation. In one embodiment useful for reducing pathogens in a plurality of fluid samples having different volumes, for example, the present invention provides an algorithm wherein net radiant energies provided to fluid samples are determined by multiplying the ratio of the volume of the fluid and the surface area of the container which transmits light to the fluid by a proportionality constant having a value greater than zero. For embodiments wherein light is delivered to samples using a constant radiant power, algorithms of the present invention are capable of using the volumes and/or masses of fluid samples to determine illumination times necessary for uniformly treating a plurality of fluid samples. Algorithms useful in the methods of the present invention may involve a large number of other variables, including but not limited to, the density of the fluid, the surface area of the container or flow reactor that transmits light to the fluid, the volume of the container holding the fluid, the agitation rate of the container, the concentration and identity of particles which absorb and/or scatter electromagnetic radiation, the composition of the fluid including the concentration and identity of blood components, the concentrations and compositions of photosensitizers added in the fluid, wavelength distribution of light delivered to the fluid, the radiant power employed during illumination, the method of fluid mixing employed, fluid dilution conditions prior to treatment with electromagnetic radiation, or any combination of these variables. Algorithms of this aspect of the present invention may be executed by a variety of processors, devices and device controllers, including microcomputers, general-purpose computers or processing systems capable of running application software.

In another aspect, the present invention provides methods of treating fluid samples in at least partially transparent containers having a fixed volume and undergoing agitation, wherein the agitation rate employed is determined on the basis of the volume of the fluid. In the context of this description, agitation rate refers to the rate in which a container is subjected to periodic displacement cycles and may be quantitatively characterized in terms of the number of agitation cycles per unit time (e.g. cycles per minute). In one embodiment, the agitation rate employed is selected to provide equivalent fluid mixing rates in a plurality of fluid samples undergoing treatment that are independent of the volumes of the samples. For example the agitation rate of the container may be positively correlated to the volume of the fluid in the container undergoing treatment. Exemplary algorithms relating container agitation rate and fluid volume useful in the present invention include, but are not limited to, substantially linear correlations, substantially exponential correlations, substantially logarithmic correlations, substantially quadratic correlations or any combination of these.

The methods and device of the present invention are broadly applicable to any process whereby a fluid undergoing processing is exposed to electromagnetic radiation. The present methods are particularly applicable to fluid treatment processes wherein uniform treatment of particles of a fluid to selected radiant energies is desirable. The present invention provides methods of reducing the biological activities of pathogens in biological fluids including blood or blood components, such as red blood cell-containing blood components, platelet containing blood components, plasma containing components, white blood cell containing components and solutions containing one or more proteins derived from blood, and in fluids which are administered as therapeutic and/or re-infusion agents, such as intravenous medicines or peritoneal solutions. The methods of the present invention also provide for effective reduction of pathogens in fluids generated from expression systems, such as recombinant expression systems. In the context of this description, the term "recombinant expression systems" may refer to cell or tissue culture systems including large scale fermentation systems. Other exemplary applications of the methods of the present invention include, but are not limited to, reducing the biological activities of leukocytes in fluids including biological fluids, fluid purification methods, methods of controlling the rates and extent of photochemical reactions in a fluid, photopolymerization techniques, and methods for regulating chemical synthesis reactions in fluids.

In another aspect, the present invention provides methods for reducing pathogens in a fluid comprising the steps of: (1) providing the fluid held in an at least partially transparent container, wherein the fluid comprises particles; (2) determining the volume of the fluid; (3) mixing the fluid held in the at least partially transparent container, optionally at a selected mixing rate; (4) calculating a net radiant energy for reducing the pathogens in the fluid using the volume and/or mixing rate of the fluid; and (3) providing electromagnetic radiation having the net radiant energy to the fluid, thereby generating a photoreactive layer in the fluid wherein the electromagnetic radiation interacts with the particles; and wherein mixing the fluid in the container transports the particles through the photoreactive layer, thereby reducing pathogens in the fluid. Optionally methods of this aspect of the present invention may further include the step of adding additives to the fluid, such as a photosensitizer.

In another aspect, the present invention provides methods for uniformly treating a plurality of fluid samples with electromagnetic radiation, the method comprising the steps of: (1) providing the plurality of fluid samples, wherein each fluid sample comprises particles; (2) determining the volumes of each of the fluid samples held in at least partially transparent containers; (3) providing each of the fluid samples held in at least partially transparent containers; (4) mixing each of the fluid samples held in the at least partially transparent containers, optionally at a selected mixing rate; (5) calculating net radiant energies for each of the fluid samples using the volumes and/or mixing rates of each of the fluid samples; and (6) providing electromagnetic radiation having the net radiant energies to each of the fluid samples, thereby generating photoreactive layers in each of the fluid samples, wherein the electromagnetic radiation interacts with the particles in photoreactive layers of each fluid sample; and wherein mixing the fluid samples transports the particles through the photoreactive layers, thereby uniformly treating the plurality of fluid samples with electromagnetic radiation. Optionally, methods of this aspect of the present invention may further include the step of adding additives to each of the fluid samples, such as photosensitizers.

BRIEF DESCRIPTION OF THE DRAWINGS

FIG. 2A is a schematic drawing illustrating an electromagnetic radiation profile at a selected wavelength for a photoreactive layer generated in a fluid undergoing treatment with electromagnetic radiation. In the plot shown in FIG. 2A, light intensity is plotted verses the distance from the illuminated surface of the fluid.

In FIG. 2B, the scale shown on the Y-axis on the right side of the graph corresponds to plot (A), the scale shown on the Y-axis on left side of the graph corresponds to plot (B) and the X-axis is in units of nanometers.

FIG. 3 is a flow diagram illustrating process steps of an exemplary method of uniformly treating a plurality of fluid samples wherein the net radiant energies exposed to individual fluid samples are determined on the basis of their calculated volumes.

DETAILED DESCRIPTION OF THE INVENTION

Figure 1:
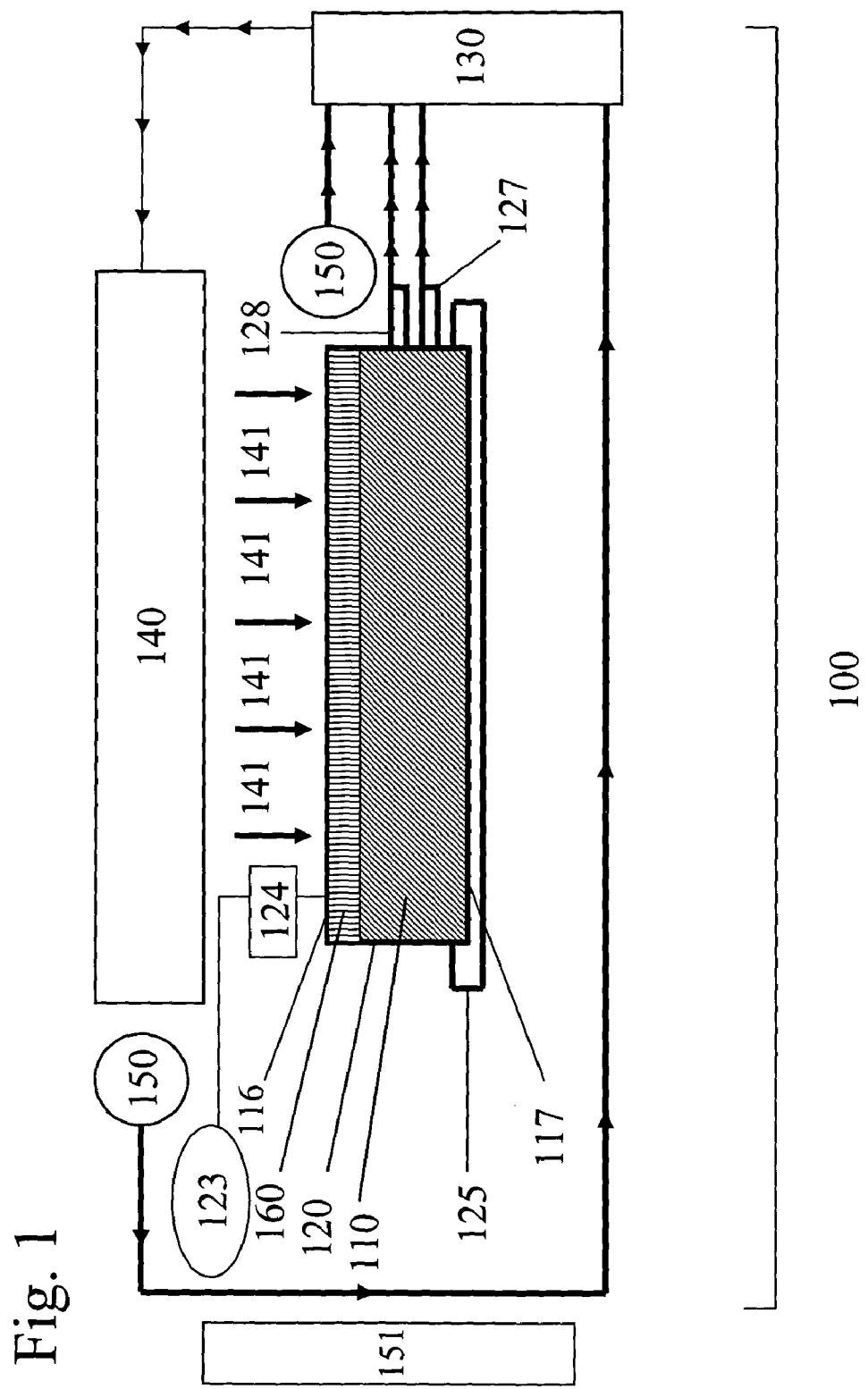
FIG. 1 is a schematic drawing of an exemplary device for reducing the biological activities of pathogens in a fluid undergoing continuous mixing.

Referring to the drawings, like numerals indicate like elements and the same number appearing in more than one drawing refers to the same element. In addition, hereinafter, the following definitions apply:

The terms "electromagnetic radiation" and "light" are used synonymously in the present description and refer to waves of electric and magnetic fields. Electromagnetic radiation useful for the methods of the present invention includes, but is not limited to ultraviolet light, visible light, and infrared light or any combination of these. Selection of the wavelength distribution of electromagnetic radiation used in the methods of the present invention may be based on a number of factors including but not limited to the absorption spectrum of one or more photosensitizers provided to the fluid undergoing treatment, the extinction coefficients of particles of the fluid undergoing treatment as a function of wavelength or a combination of these. Exemplary fluid treatment methods may use electromagnetic radiation characterized by a distribution of wavelengths that are substantially absorbed by photosensitizers added to the fluid. Exemplary methods and devices of the present invention useful for treating red blood cell-containing blood components use electromagnetic radiation having wavelengths in the visible region of the electromagnetic spectrum. For example, in one aspect of the present invention useful for treating red blood cell-containing fluids and employing a photosensitizer such as a material which absorbs light in the visible region of the electromagnetic spectrum, electromagnetic radiation having a distribution of wavelengths selected over the range of about 400 nm to about 800 nm may be employed. Exemplary methods and devices of the present invention useful for treating plasma and platelet-containing blood components may use electromagnetic radiation having wavelengths in the ultraviolet region of the electromagnetic spectrum. For example, in one aspect of the present invention which may be useful for treating platelet and plasma-containing fluids electromagnetic radiation having a distribution of wavelengths selected over the range of about 300 nm to about 400 nm may be employed. As will be understood by persons skilled in the art, the absorption spectrum of photosensitizers may vary when in the presence of certain particles, such as proteins, and the present methods may take this change in the absorption spectrum of photosensitizer into account in the selection of the appropriate distribution of wavelengths of electromagnetic radiation delivered to a fluid undergoing treatment.

"Net radiant energy" refers to the total amount of radiant energy delivered to a fluid during a fluid treatment process or combination of fluid treatment processes. Net radiant energy may be expressed in terms of power, exposure time and illuminated surface area by the equation;

$$E_{net} = \int_{A=0}^{A=A_I} \int_{t=0}^{t=t_f} P(t, A) dA dt; \quad (I)$$

wherein $E_{net}$ is the net radiant energy delivered, P(t) is the power of the electromagnetic radiation exposed to the fluid as a function of time and area, $t_f$ is the time interval for illumination, t is time, A is area and $A_I$ is the illuminated area of the container holding the fluid. In methods of the present invention employing a substantially constant power, net radiant energy may be expressed in terms of radiant power and exposure time by the equation:

$$E_{net} = P \times t_f; \quad (II)$$

wherein $E_{net}$ is the net radiant energy, P is the constant radiant power of the electromagnetic radiation and $t_f$ is the time interval for illumination. Net radiant energy may also be expressed per unit area or per unit volume.

"Treating a fluid with electromagnetic radiation" refers to a process whereby electromagnetic radiation is delivered to a fluid to achieve a desired change in the composition of the fluid or particles comprising the fluid and/or to achieve a change in the biological activities of one or more particles of the fluid. In one aspect, the methods of the present invention are capable of uniformly treating a plurality of fluids with electromagnetic radiation to uniformly reduce the biological activities of pathogens present in the fluids.

"Substantially linear manner" refers to changes of one or more variables which may be represented by a linear relationship. Variation of a parameter in a substantially linear manner is intended to include some deviation from absolute linear variation. In one embodiment, variation of a parameter in a substantially linear manner includes deviations from absolute linearity less than 10% over the relevant range of values, and preferably less than 5% for some fluid treatment applications.

The terms "intensity" and "intensities" refers to the square of the amplitude of an electromagnetic wave or plurality of electromagnetic waves. The term amplitude in this context refers to the magnitude of an oscillation of an electromagnetic wave. Alternatively, the terms "intensity" and "intensities" may refer to the time average energy flux of a beam of electromagnetic radiation or plurality of beams of electromagnetic radiation, for example the number of photons per square centimeter per unit time of a beam of electromagnetic radiation or plurality of beams of electromagnetic radiation.

"Substantially exponential manner" refers to changes of one or more variables which may be accurately represented by an exponential relationship. Variation of a parameter in a substantially exponential manner is intended to include some deviation from absolute exponential variation. In one embodiment, variation of a parameter in a substantially exponential manner includes deviations from purely exponential behavior less than 10% over the relevant range of values, and preferably less than 5% for some fluid treatment applications.

"Mixing rate" refers to the rate in which particles comprising a fluid are internally circulated or transported during treatment with electromagnetic radiation. In one aspect of the present invention, fluid mixing rate relates to the rate in which particles comprising a fluid are transported into and out of one or more photoreactive layers formed upon illumination with electromagnetic radiation.

"Particles comprising a fluid" refers to materials that make up a fluid undergoing treatment. Particles of a fluid include, but are not limited to, molecules, ions, cells, fragments of cells, plasma, proteins, peptides, nucleic acids, oligonucleotides, biopolymers, solvent, additives, water, photosensitizers, pathogens, aggregates of molecules and complexes, aggregates of pathogens, leukocytes or any combinations of these. In some embodiments of the present invention, equivalent effective net radiant energies are provided to substantially all particles comprising a fluid undergoing treatment. In the context of this aspect of the present invention, "substantially all particles of a fluid" refers to more than at least 99% of the particles comprising the fluid of a fluid, and preferably for some applications refers to more than at least 99.5% of the volume of a fluid.

"Photosensitizers" refer to materials that absorb electromagnetic radiation at an appropriate wavelength or range of wavelengths and utilize the absorbed energy to carry out desired chemical and/or physical processes. Photosensitizers for blood treatment applications are capable of initiating a reduction in the biological activities of pathogens present in a fluid upon absorption of electromagnetic radiation. Photosensitizers useful for some applications of the present invention include compounds that preferentially bind to, absorb or intercalate into nucleic acids, thereby focusing their photodynamic effects upon microorganisms, such as pathogenic microorganisms. Exemplary photosensitizers useful in the present methods include, but are not limited to, alloxazine compounds, isoalloxazine compounds, 7,8-dimethyl-10-ribityl isoalloxazine, porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers useful in certain applications include, but are not limited to, nontoxic, endogenous photosensitizers that do not require removal from a biological fluid comprising therapeutic and/or re-infusion agents prior to administration into a patient. Photosensitizers may be present in fluids in ionized, partially ionized and/or neutral states. Photosensitizers may be present in fluids as aggregates of compounds and molecular complexes.

The term "endogenous" means naturally found in a human or mammalian body, either as a result of synthesis by the body or due to ingestion as an essential foodstuff (e.g. vitamins) or formation of metabolites and/or byproducts in vivo. The term "non-endogenous" means not naturally found in a human or mammalian body, either as a result of synthesis by the body or due to ingestion of an essential foodstuff or formation of metabolites and/or byproducts in vivo.

"Enhancer" refers to materials added to a fluid undergoing treatment to make the desired treatment process more efficient and selective. Enhancers include antioxidants or other agents added to prevent degradation of fluid components comprising therapeutic and/or re-infusion agents. In addition, enhancers include materials which improve the rate of reduction of the biological activities of pathogens and/or leukocytes. Exemplary enhancers include, but are not limited to, adenine, histidine, cysteine, propyl gallate, glutathione, mercaptopropionylglycine, dithiothreotol, nicotinamide, BHT, BHA, lysine, serine, methionine, gluscose, mannitol, trolox, glycerol and any combination of the compounds.

"Fluid" refers to any material which is capable of conforming to the shape of a container in which it is held. Fluids useable with methods of the present invention include, but are not limited to, liquids, and mixtures of more than one liquid, colloids, foams, emulsions, sols, and any combination of these. Fluids are comprised of particles. Exemplary fluids useable in the methods of the present invention include biological fluids, such as whole blood, blood components, blood subcomponents, plasma-containing blood components, platelet-containing blood components, red blood cell-containing blood components, white blood cell-containing blood components, solutions containing one or more proteins derived from blood, or any combinations of these. Exemplary fluids also comprise, but are not limited to, peritoneal solutions used for peritoneal dialysis, intravenous medicines, injectable medicines, nutritional fluids, food stuffs, fermentation media generated from recombination methods, materials produced by recombinant techniques including therapeutic and diagnostic materials, materials produced from transgenic animals and plants including therapeutic and diagnostic materials, milk and milk products, water, fruit juices, broths, soups, beverages, chemical and pharmaceutical products, and vaccines.

"Blood," "blood product" and "blood component" as used herein include whole blood, blood components and materials which may be derived from whole blood or a component thereof. "Blood," "blood product" and "blood component" as used herein also include blood, blood components and/or blood products treated with one or more additives, such as an anticoagulant agent, enhancer, photosensitizer, preservative or diluent. "Blood," "blood product" and "blood component" also refer to mixtures of these materials and additives, such as photosensitizers, enhancers, stabilizers, anticoagulant agents and preservatives. Cellular blood components include, but are not limited to erythrocytes (red blood cells), leukocytes (white blood cells), thrombocytes (platelets), esinophils, monocytes, lymphocytes, granulacytes, basophils, plasma, and blood stems cells. Non-cellular blood components include plasma, and blood proteins isolated from blood samples including, but not limited to, factor III, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen, streptokinase complex, ceruloplasmin, transferrin, haptoglobin, antitrypsin and prekallikrein.

"Substantially logarithmic manner" refers to changes of one or more variables which may be accurately represented by a logarithmic relationship (i.e. $y=a\ e^x$). Variation of a parameter in a substantially logarithmic manner is intended to include some deviation from absolute logarithmic variation. In one embodiment, variation of a parameter in a substantially logarithmic manner includes deviations from purely logarithmic behavior less than 10% over the relevant range of values, and preferably less than 5% for some fluid treatment applications.

"Effective net radiant energies" refers to the net radiant energies exposed to particles of a fluid undergoing mixing during treatment of the fluid with electromagnetic radiation. In one embodiment, the effective net radiant energy provided to a particle is the integrated radiant energy exposed to a particle as it is transported into and out of a photoreactive layer during illumination of the fluid with electromagnetic radiation. "Equivalent effective net radiant energies" is intended to include some deviations from absolutely equivalence. In an exemplary embodiment, for example, exposure to equivalent effective net radiant energies corresponds to illumination and mixing conditions whereby particles of a fluid are exposed to approximately the same effective net radiant energies during treatment with electromagnetic radiation with deviations from absolutely equivalence less than 20%, preferably for some applications less than 10%, and more preferably for some applications less than 5%.

"Pathogenic contaminants" and "pathogens" are used synonymously and refer to viruses, bacteria, bacteriophages, fungi, protozoa, and blood-transmitted parasites. Exemplary viruses include acquired immunodeficiency (HIV) virus, hepatitis A, B, C and G viruses, sindbis virus, cytomegalovirus, vesicular stomatitis virus, herpes simplex viruses, human T-lymphotropic retroviruses, HTLV-III, lymphadenopathy virus LAV/IDAV, parvovirus, transfusion (TT) virus, Epstein-Barr virus, West Nile virus and others known to the art. Exemplary bacteriophages include but are not limited to ΦX174, Φ6, λ, R17, T4 and T2. Exemplary bacteria include *P. aeruginosa, S. aureus, S. epidermidis, L. monocytogenes, E. coli, K pneumonia, B. cereus, Y. enterocolitica*, and *S. marcescens*. Exemplary parasites include malaria, babesia, chagas and trypanosome.

"Biologically active" refers to the capability of a composition, material, cell, microorganism, or pathogen to affect a change in a living organism or component thereof.

"Nucleic acid" includes both ribonucleic acid (RNA) and deoxyribonucleic acid (DNA).

"Partially transparent" refers to the property of a material, device or device component which when illuminated transmits intensities of at least a portion of incident electromagnetic radiation. Partially transparent materials useful in the present invention are capable of transmitting incident electromagnetic radiation in a manner providing radiant intensities in a photoreactive layer of a fluid which are sufficient to induce desired chemical and/or physical changes in the fluid. Partially transparent materials may transmit at least a portion of electromagnetic radiation having wavelengths absorbed by photosensitizers and nucleic acids and may absorb, transmit and/or scatter electromagnetic radiation of other wavelengths. Partially transparent also refers to materials having at least one partially transmissive region and at least one absorbing or scattering region. Exemplary partially transparent materials include, but are not limited to, polycarbonate, glass, quartz, polstyrene, polyvinyl chloride, polyolefin, polymethlamethacrylate, cellulose acetate butyrate, glycol modified polyethylene terphthalate, polychlorotrifluooethylene or any combinations of these materials.

"Pathogen reduction" and "reducing pathogens" are used synonymously in the present description and refer to processes which partially or totally prevent pathogens from reproducing. Pathogen reduction may occur by directly killing pathogens, interfering with their ability to reproduce, or a combination of killing pathogens and interfering with their ability to reproduce. Pathogen reduction reduces the biological activities of pathogens present in a fluid.

"Substantially quadratic manner" refers to changes of one or more variables which may be accurately represented by a quadratic relationship (i.e. $y=ax^2+bx+c$). Variation of a parameter in a substantially quadratic manner is intended to include some deviation from absolute quadratic variation. In one embodiment, variation of a parameter in a substantially quadratic manner includes deviations from purely quadratic behavior less than 10% over the relevant range of values and preferably less than 5% for some fluid treatment applications.

"Photoreactive layer" refers to a layer positioned adjacent to a illuminated surface of fluid having intensities of electromagnetic radiation that are sufficient to initiate chemical and/or physical changes in the fluid at a rate large enough for a selected fluid treatment application. In one embodiment useful for reducing pathogens in fluids, the photoreactive layer has a thickness equal to a penetration depth corresponding to the distance from an illuminated surface of a fluid to a point in the fluid wherein the intensity of electromagnetic radiation equals 10% of the intensity of electromagnetic radiation at the illuminated surface of the fluid. The present invention includes methods wherein illumination of a fluid generates a photoreactive layer that extends partially or fully through the volume of a fluid.

"Optical communication" refers to the orientation of two or more elements such that light is capable of propagating from one element to another element. Elements can be in optical communication via one or more additional elements such as reflectors, lenses, fiber optic couplers, wave guides or any combinations of these.

In the following description, numerous specific details of the devices, device components and methods of the present invention are set forth in order to provide a thorough explanation of the precise nature of the invention. It will be apparent to those of skill in the art, however, that the invention can be practiced without these specific details.

This invention provides methods, devices and device components for uniformly treating fluid samples with electromagnetic radiation. In particular, the present invention provides methods and devices for uniformly treating a plurality of samples comprising biological fluids such that each sample undergoes equivalent treatment. Method of the present invention are useful for reducing the biological activities of pathogens throughout entire volumes of a fluids, thereby generating treated fluids having comparable levels of pathogens and having components comprising therapeutic and/or re-infusion agents with comparable biological activities and vitalities.

FIG. 1 schematically illustrates an exemplary fluid treatment system 100 for uniformly treating fluid samples with electromagnetic radiation. Referring to FIG. 1, fluid 110 is held in an at least partially transparent container 120. The container 120 is operationally connected to a means of mixing 125 capable of continuously mixing fluid 110 at a selected, constant fluid mixing rate or at a mixing rate that is selectively adjusted during illumination. Optionally, container 120 may be operationally connected to reservoir 123 via fluid valve 124 for the introduction of additives, such as photosensitizers, to the fluid prior to, during or after treatment with electromagnetic radiation. Electromagnetic radiation source 140 is provided and positioned in optical communication with fluid 110. The present invention includes embodiments having a plurality of electromagnetic radiation sources 140 positioned such that they illuminate a plurality of different surfaces of container 120, such as device configurations wherein the top 116 and bottom 117 of container 120 are illuminated simultaneously. Electromagnetic radiation source 140 is operationally connected to electromagnetic radiation source controller 130, which is capable of determining net radiant energies, radiant powers and/or illumination times required to uniformly treat a plurality of fluid samples, including fluid samples having different volumes and/or masses and fluid samples undergoing mixing at different mixing rates. Electromagnetic radiation source controller 130 may be configured such that it can selectively adjust the radiant power of electromagnetic radiation source 140 or adjust the illumination period in which container 120 is exposed to electromagnetic radiation.

Optionally, electromagnetic radiation source controller 130 may also be operationally connected to detectors 150 capable of measuring the net radiant energies, and/or radiant powers generated by electromagnetic radiation source 140 as a function of time. Exemplary detectors 150 are in optical communication with electromagnetic radiation source 140 and are capable of generating output signals (schematically represented by arrows in FIG. 1) which provide measurements corresponding to net radiant energies and/or radiant powers to electromagnetic radiation source controller 130. In an exemplary embodiment, detectors 150 are capable of providing a measurements of the net radiant energy exposed to a fluid during an illumination period. In another embodiment, detectors 150 and electromagnetic radiation source controller 130 are configured to provide closed loop feedback control of electromagnetic radiation source 140 necessary for maintaining a constant radiant power for a selected illumination period and/or for providing a selected net radiant energy to a fluid sample.

Fluid treatment system 100 may optionally include the means of determining the volume and/or mass of fluid 127 and/or the means of determining the fluid mixing rate 128. In an exemplary embodiment, the means of determining the volume an/or mass of fluid 127 and/or the means of determining the fluid mixing rate 128 are operationally connected to electromagnetic radiation source controller 130. In this embodiment, the means of determining the volume and/or mass of fluid 127 and the means of determining the fluid mixing rate 128 are capable of generating output signals (schematically represented by arrows in FIG. 1) which provide electromagnetic radiation source controller 130 input parameters, such as the volume, mass and/or mixing rate, useful for determining the net radiant energies necessary for uniformly treating fluid samples. Fluid treatment system 100 may also optionally include fluid cooling system 151 operationally connected to container 120 and capable of maintaining a fluid temperature below predetermined limits during a selected illumination time. Exemplary fluid cooling systems 151 include force convection cooling systems.

In one embodiment, electromagnetic radiation source controller 130 determines net radiant energies for uniform treatment of fluids 110 based on the volume of the fluid 110, mass of fluid 110, the selected mixing rate provided by means of mixing 125 or any combination of these parameters. In an embodiment of the present invention wherein electromagnetic radiation is provided to fluid 110 using a constant radiant power, electromagnetic radiation source controller 130 determines illumination times necessary for providing uniform treatment of a plurality of fluid samples. In one embodiment, electromagnetic radiation source controller 130 receives input parameters from the means of determining the volume and/or mass of fluid 127 and/or the means of determining the fluid mixing rate 128, which are used in an algorithm that determines net radiant energies, radiant powers and illumination times necessary for providing uniform treatment with electromagnetic radiation. Alternatively, electromagnetic radiation source controller 130 receives input parameters from an operator or user, which are used to determine net radiant energies, radiant powers and illumination times.

Electromagnetic radiation source controller 130 generates control signals (schematically represented by arrows in FIG. 1) which are transmitted to electromagnetic radiation source 140. Control signals are received by electromagnetic radiation source 140, which exposes fluid 110 to the selected net radiant energy calculated by electromagnetic radiation source controller 130. Means of mixing 125 provides continuous fluid mixing of fluid 110 in container 120 at a selected fluid mixing rate during exposure of fluid 110 to the selected net radiant energy. In an exemplary embodiment, electromagnetic radiation source 140 provides a selected net radiant energy to fluid 110 for a selected illumination time. In FIG. 1, the radiant energy provided to fluid 110 is schematically depicted by arrows 141. Exposure of fluid 110 to electromagnetic radiation occurs in a photoreactive layer 160 (not drawn to scale in FIG. 1) proximate to the illuminated surface of fluid 110. Within the photoreactive layer 160, electromagnetic radiation interacts with particles comprising fluid 110, thereby initiating chemical and/or physical changes in fluid 110. Exposure of substantially all particles of fluid 110 to equivalent effective net radiant energies is provided by transporting the particles comprising fluid 110 through the photoreactive layer 160 via mixing.

In the present invention, the detectors 150 may be used to monitor and assist in delivering a selected radiant power during illumination. Detectors 150 may also provide in situ radiant power measurements useful for determining an illumination time which is needed to expose particles of fluid 110 to equivalent effective net radiant energies. The present invention includes embodiments wherein output signals provided by the detectors 150 represent radiant energies and radiant powers actually exposed to fluid 110 and, therefore, include corrections to account for absorption and scattering by the at least partially transparent container 120.

An illuminated fluid may be characterized in terms of an electromagnetic radiation intensity profile corresponding to the intensities of electromagnetic radiation in an illuminated fluid as a function of distance from the surface of the fluid that is illuminated with electromagnetic radiation. FIG. 2A shows an exemplary electromagnetic radiation intensity profile for a selected wavelength of incident electromagnetic radiation penetrating a fluid sample. The electromagnetic radiation profile shown illustrates a photoreactive layer (schematically illustrated in FIG. 1 as drawing element 160) of the present invention. In the plot shown in FIG. 2A, light intensity is plotted verses the distance from the illuminated surface of the fluid. The electromagnetic radiation intensity profile illustrated in FIG. 2A is characterized by a high radiant intensity at the illuminated surface of the fluid which decreases as a function of penetration depth. The intensity gradient shown in FIG. 2A is a result of absorption and/or scattering of light by particles in the fluid. In the case of pathogen reduction in fluids comprising concentrated absorbing and/or scattering materials, such as red blood cells and platelets, the observed decrease in intensity is often very rapid, thereby generating a very thin photoreactive layer (thickness<2 mm). The present invention includes methods, however, wherein the photoreactive layer formed upon illumination is defined by an intensity gradient extending through the entire volume of a fluid sample that is not highly scattering or absorbing, such as plasma sample. In these embodiments, mixing is useful for exposing substantially all the particles of the fluid to equivalent effective net radiant energies, despite the existence of the intensity gradient. Optical configurations providing a plurality of illuminated surfaces and resulting in a plurality of photoreactive layers are also useful in the methods of the present invention.

Figure 2B:
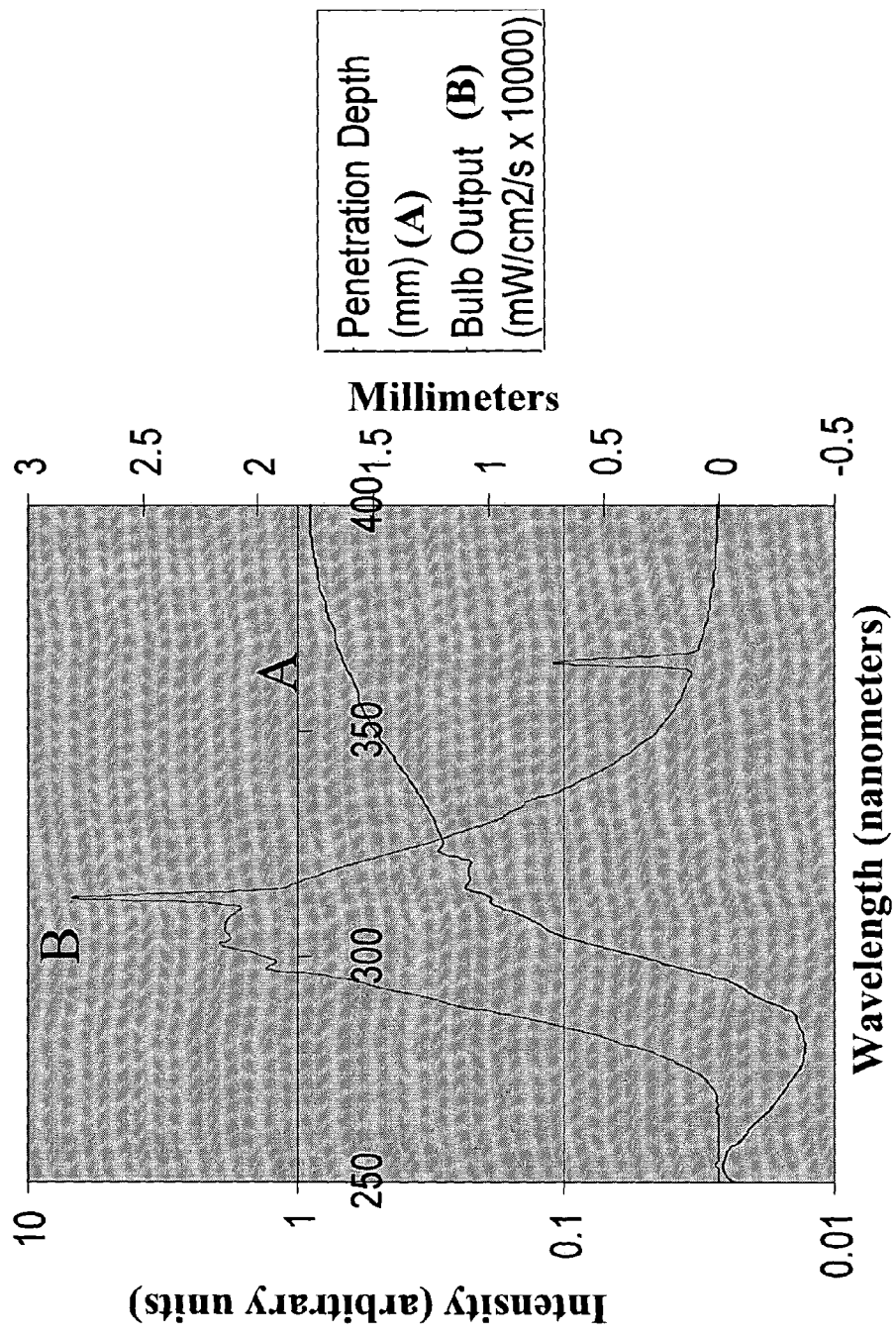
FIG. 2B shows a plot (A) of penetration depth (Y-axis, millimeters) as a function of wavelength (X-axis) and a plot (B) of the radiant output of an exemplary source of electromagnetic radiation (Y-axis) as a function of wavelength (X-axis).

FIG. 2B shows a plot (A) of penetration depth as a function of wavelength for a platelet and plasma-containing fluid illuminated with electromagnetic radiation. In the context of this description, "penetration depth" refers to the distance from an illuminated surface of a fluid to the point in the fluid wherein the light intensity equals 10% of the intensity of light at the surface. Also shown in FIG. 2B is a plot (B) of the radiant output of an exemplary source of electromagnetic radiation as a function of wavelength. As shown in FIG. 2B, different wavelengths of incident electromagnetic radiation are characterized by different penetration depths due to the wavelength dependent absorption and scattering processes by the particles fluid comprising the fluid.

The methods of the present invention may optionally include the step of determining the volume of the fluid. Any means of determining volume known in the art are useable in the present invention. In an exemplary embodiment, the mass of the fluid sample is determined using a weighing device, such as a scale or mass balance. Specifically, the mass of fluid 110 is determined and the measured mass is divided by the density of the fluid to determine fluid volume. For example, the volume of a fluid comprising a mixture of platelets in blood plasma may be calculated from the measured fluid mass via the equation:

$$\text{Volume} = \frac{(\text{mass})}{(\text{density})} = \frac{\text{mass (g)}}{1.026 \left(\frac{g}{ml}\right)}. \qquad (III)$$

The density used in volume calculations may account for steps involving fluid dilution and the addition of one or more additives, such as photosensitizers, enhancers, anticoagulant agents, diluents and/or preservatives. The density used in volume calculations in the present invention may be an approximate density of fluid 110, for example within 5% of the actual density or within 1% of the actual density. The present invention includes methods wherein the volume used for calculation of net radiant energies is corrected to reflect the addition of additives to the fluid undergoing treatment.

In one aspect of the present invention providing uniform treatment of fluid samples with electromagnetic radiation, the net radiant energy delivered to fluid 110 to achieve pathogen reduction is determined by operation of an algorithm which directly relates net radiant energy to the volume of fluid 110. In an exemplary embodiment, for example, the net radiant energy is linearly related to volume by the equation:

$$\text{Net Radiant Energy} = (Z) \times \left(\frac{V}{A}\right) + (b); \qquad (IV)$$

wherein net radiant energy is in units of joules per centimeter squared, V is volume, Z is a proportionality constant having a value greater than 0 and units of joules per unit volume, A is the surface area of the container or flow reactor which transmits electromagnetic radiation to the fluid from one or more electromagnetic radiation source and b is a constant in units of joules per centimeter squared. In some embodiments, the surface area of the container or flow reactor that transmits electromagnetic radiation to the fluid (A) is reduced due to the presence of a label or other nontransmissive element that prevents transmission of light. In these embodiments, therefore, the value of A in Equation IV takes the presence of the label into account. In the present invention, the values of Z and b may depend on a large number of variables including, but not limited to, the composition of fluid undergoing treatment, amount of pathogens in the fluid, the desired level of pathogen/reduction the optical geometry, means of fluid mixing and fluid mixing, transparency, shape, volume and/or surface area of the container, or any combination of these parameters. In an exemplary embodiment useful for treatment of plasma and platelet containing fluids having volumes greater than about 200 milliliters and less than about 400 milliliters contained in a 1-liter container, Z has a value of about 6.24 J ml$^{-1}$ and b has a value of about 0.

The methods of the present invention may optionally include the step of adding an effective amount of one or more additives to the fluid 110 undergoing treatment. In the context of the present invention the term additive includes, but is not limited to, photosensitizers, enhancers, stabilizers, anticoagulant agents, diluents, preservatives and all combinations of these. In the present invention, additives may be introduced to the fluid using a suitable carrier fluid such as water, salt solution or buffer, and additives may be added to fluid 110 prior to placement of the fluid into container 120. Alternatively, additives may be added to fluid 110 in the container 120 from reservoir 123. Additives may be added to a fluid undergoing treatment prior to placing the fluid in the container or may be separately flowed into the container prior to, during or after illumination with electromagnetic radiation. In one embodiment, photosensitizers are added to an anticoagulant agent and the mixture of photosensitizer and anticoagulant are added to fluid 110. In an exemplary embodiment, photosensitizers of the present invention are uniformly mixed throughout the entire volume of fluid 110 prior to and during illumination with electromagnetic radiation.

The methods of the present invention may optionally further comprise the step of adding a diluent to the fluid 110 prior to treatment with electromagnetic radiation. Dilution prior to treatment may be useful for selectively adjusting the optical depth of a fluid undergoing treatment and, thereby controlling the thickness of photoreactive layers in the fluid formed upon illumination. Dilution of a fluid prior to treatment may also be useful for selectively adjusting the concentration of additives in a fluid such as photosensitizers, enhancers, preservatives, and anticoagulation agents.

FIG. 3 is a flow diagram illustrating process steps of an exemplary method of uniformly treating a plurality of fluid samples wherein the net radiant energies exposed to individual fluid samples are determined on the basis of their calculated volumes. As shown in FIG. 3, a fluid sample in an at least partially transparent container is provided for uniform treatment with electromagnetic radiation. Optionally, additives are provided to the fluid, including addition of photosensitizers and/or anticoagulation agents. Optionally, the fluid is diluted to achieve a desired optical thickness. Referring again to FIG. 3, the mass of the fluid sample, including any additives if added, is measured and used to calculate the volume of the fluid by dividing the measured mass by an estimated density of the fluid. The estimated density used in this calculation takes into consideration the amount of any additives provided to the fluid undergoing treatment.

Referring again to the flow diagram in FIG. 3, a net radiant energy necessary for providing uniform treatment of the fluid sample is determined on the basis of the calculated volume of the fluid, including any additives provided to the fluid such as photosensitizers, anticoagulation agents and/or diluents. The mixture is continuously mixed at a selected fluid mixing rate and exposed to the net radiant energy necessary for providing uniform treatment. Two methods of exposing the sample to the net radiant energy necessary for providing uniform treatment are shown in FIG. 3. In one embodiment, the net radiant power provided to the fluid is monitored as a function of time. When the net radiant power provided to the fluid is equal to or within a specified range of the determined net radiant energy for providing uniform treatment a control signal is generated that stops exposure of the sample to electromagnetic radiation. Alternatively, the illumination period necessary for providing uniform treatment is calculated for a selected, constant radiant power and the fluid sample is exposed to the selected, constant radiant power for a the calculated illumination period. Optionally, closed loop feedback control may be employed to maintain a constant radiant power for the duration of a selected illumination period based on real time measurements of radiant power. In both methods, exposure of the sample to electromagnetic radiation is stopped, for example by turning off the source of electromagnetic radiation, when the sample has been exposed to the net radiant energy necessary for providing uniform treatment with electromagnetic radiation. As shown in the flow diagram in FIG. 3, after treatment of the fluid sample, new fluid samples are provided and the series of processing steps is repeated for all fluid samples undergoing uniform treatment with electromagnetic radiation.

Selection of a radiant power and illumination time necessary to deliver the desired net radiant energy also establishes the rate in which radiant energy is introduced to the photoreactive layer. The present invention includes methods wherein the rate of fluid mixing and the rate of delivering radiant energy to the photoreactive layer are positively correlated to avoid under exposure and/or over exposure of fluid components comprising therapeutic and/or re-infusion agents to electromagnetic radiation. Methods of the present invention employing radiant powers and illumination times selected on the basis of the fluid mixing rate, the volume of the fluid, the mass of the fluid or any combination of these provide methods of selectively controlling the rates of photochemical changes occurring in a fluid. In exemplary fluid treatment methods of the present invention, larger radiant powers and shorter illumination times are employed for smaller volume samples which exhibit more rapid circulation of particles into and out of the photoreactive layer than larger volume samples which exhibit less rapid circulation of particles into and out of the photoreactive layer. Smaller radiant powers and longer illumination times are employed for larger volume samples which exhibit slower circulation of particles into and out of the photoreactive layer than smaller volume samples which exhibit faster circulation of particles into and out of the photoreactive layer.

The methods of the present invention are well suited for the treatment of fluids, contained in an at least partially transparent fixed-volume container. In this context the term "fixed volume container" refers to a closed space, which may be made of a rigid or flexible material. Containers useful in the methods of the present invention may have any volume, size, surface area and shape. Containers useful for some applications are highly transparent in at least one region, for example having a percentage transmission greater than or equal to 70% with respect to electromagnetic radiation having wavelengths which are capable of directly reducing pathogens and/or exciting photosensitizers present in the fluid. Containers useful in the present methods and devices may have a single transparent surface for transmitting electromagnetic radiation or may have a plurality of transparent surfaces. Materials for making containers, physical dimensions of containers and optical geometries of container and electromagnetic radiation sources useable in the present invention may be easily determined by those having skill in the art without undue experimentation.

The methods and devices of the present invention are also applicable to treatment of fluids flowing through a flow-through reactor. In one embodiment, a fluid is conducted through a flow-through reactor, wherein the fluid undergoes fluid mixing and is exposed to a net radiant energy necessary for providing uniform treatment with electromagnetic radiation. In one embodiment, fluid is flowed through the flow-through reactor at a flow velocity selected to establish a residence time of the fluid in the illuminated regions of the flow-through reactor providing a desired extent of reduction in the biological activities of pathogens present. Flow-through reactors useful in the present methods include, but are not limited to, open or closed containers having one or more openings to allow flow-through of fluid therein. Exemplary flow-through reactors include tubes, channels, troughs, microchannels, thin film flow-through and all equivalents devices and device components known in the art. Mixing in flow through treatment applications may be provided by any means known in the art including, but not limited to, the use of stirring devices, agitators, static mixers, fluid circulators or any combination of these devices and respective fluid mixing methods. Fluid mixing may also be provided by establishing turbulent flow conditions in the flow reactor. As will be understood by a person skilled in the art, the present invention may be practiced using a wide range of flow reactor geometries, flow reactor volumes, fluid flow rates and fluid residence times.

In the present invention, radiant energy may be provided to fluids undergoing treatment by any means known in the art. The term "electromagnetic radiation source" refers to any device or material capable of generating electromagnetic radiation or a plurality of devices or materials capable of generating electromagnetic radiation. Exemplary electromagnetic radiation sources useable in the methods and devices of the present invention are capable of providing electromagnetic radiation to a biological sample undergoing treatment, particularly light having a selected distribution of wavelengths in the visible region, ultraviolet region or both that is selected to excite one or more photosensitizers present in the fluid. Radiant energy may be provided to a fluid sample using a single source of electromagnetic radiation or plurality of sources of electromagnetic radiation. Exemplary electromagnetic radiation sources useable in the present invention include, but are not limited to, fluorescent lamps, mercury vapor fluorescent lamps, cold cathode fluorescent lamps, excimer lamps, light emitting diodes, arrays of light emitting diodes, arc discharge lamps, tungsten-filament lamps or any combination of these. Electromagnetic sources of the present invention may include additional devices and device components for directing, attenuating, filtering and focusing electromagnetic radiation including, but not limited to, light guides, lenses, optical filters, reflectors and any combination of these. Exemplary electromagnetic radiation sources provide light having wavelengths selected over the range of about 200 nm to about 800 nm.

Any means of mixing a fluid known in the art is useable in the present invention which is capable of systematically circulating particles into and out of photoreactive layers in a fixed volume container or flow reactor. Means of mixing that provide a selected, constant fluid mixing rate or a selectively adjustable fluid mixing rate are useful for some applications. Exemplary means of mixing a fluid include, but are not limited to, agitators, stirring devices, circulators, mixers, shakers, oscillators, churning devices, oscillators, static mixers, or any combination of these. Exemplary means of mixing also include fluid recirculation devices, which achieve transport of particles into and out of the photoreactive layer via recirculating particles throughout different regions of the container or flow reactor. Exemplary static mixers useable in the present invention are described in International Application Nos. PCT/GB99/03082, PCT/GB01/01426, and PCT/EP01/13058, and in U.S. patent application Ser. No. 10/196,020, which are hereby incorporated by reference in their entireties to the extent not inconsistent with the disclosure herein. In the context of the present invention, an "agitator" refers to an apparatus which agitates a container containing the fluid, for example at a selected agitation rate. Exemplary agitators shake a container with respect to one or more dimensions or rotate the container using circular, elliptical, or other orbital motions. An exemplary agitator useful in the present invention comprises a Helmer platelet incubator/agitator (Helmer Company, Noblesville, Ind.).

Any electromagnetic radiation source controller known in the art may be used in the present invention which is capable of calculating a net radiation energy, radiant power, illumination time or any combination of these parameters based on fluid volume, fluid mixing rate or both. In an embodiment, the electromagnetic radiation source controller is also capable of establishing and maintaining a substantially constant radiant power to within about 10% for a selected illumination time, and more preferably to within about 5% for some applications of the present methods. Exemplary electromagnetic radiation source controllers of the present invention include, but are not limited to, microcomputers computers, such as an IBM personal computer or suitable equivalent thereof, work station computers, processors, microprocessor, adjustable current ballasts and all hardware equivalents.

The present methods and devices of the present invention are amenable to computer assisted automation and, thus, are well suited to high throughput treatment of a large number of fluid samples. While it is preferred for some applications of the present invention that a computer be used to accomplish many of the steps of the present methods, it is contemplated that a computer may be used to perform only a certain step or selected series of steps in the present methods.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. Methods and devices useful for the present methods can include a large number of optional device elements and components including, but not limited to temperature sensors, temperature controllers, optical filters, lens and reflectors, disposable containers and tubing, valves and pumps.

All references cited in this application and all references cited within these references are hereby incorporated in their entireties by reference herein to the extent that they are not inconsistent with the disclosure in this application. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques specifically described herein are intended to be encompassed by this invention.

Example 1

Pathogen Reduction in Fluids comprising Platelet and Plasma-Containing Blood Components The ability of the methods and devices of the present invention to uniformly treat fluid samples with electromagnetic radiation for reducing pathogens in human blood components was verified by experimental studies. Specifically, it is a goal of the present invention to provide methods of treating fluid samples comprising blood components with electromagnetic radiation such that the treated samples have comparable levels of pathogens, preferably levels low enough so that the treated samples are useful as therapeutic and/or re-infusion agents. Further, it is a goal of the present invention to provide methods of treating blood components with electromagnetic radiation which provide cellular and noncellular blood components exhibiting uniform properties, such as high biological activities and viabilities.

To achieve the aforementioned goals, the cell quality and extent of pathogen reduction in human platelet and plasma-containing blood components treated by the methods of the present invention was determined for a variety of illumination conditions and fluid mixing conditions. Platelet and plasma-containing fluid samples having volumes selected over the range of about 200 ml to about 400 ml were illuminated in 1 liter fixed volume, partially transparent containers. Prior to illumination, approximately 30 milliliters of a $5.00 \times 10^{-4}$ M solution of 7,8-dimethyl-10-ribityl isoalloxazine in normal saline was added to each platelet and plasma-containing fluid.

Electromagnetic radiation was provided by two banks of six mercury vapor fluorescent lamps (model number XG25T8E; distributed by Ushio Nichia NP-803 phosphor) positioned above and below the fluid containers. This optical geometry defines two photoreactive layers having thicknesses equal to approximately 1 millimeter corresponding to the top and bottom illuminated surfaces of the fluid. The combination of fluorescent lamps generated a radiant power of about 0.6 J cm$^{-2}$ min$^{-1}$ for an illumination time selected over the range of about 7 minutes to about 10 minutes. Radiant power was monitored in situ by photodiode light detectors, and was observed to vary less than about 0.1% over a selected illumination time after reaching steady state. The electromagnetic radiation provided to the fluid samples has a distribution of wavelengths ranging from about 265 nm to about 375 nm and a center wavelength of about 306-308 nm corresponding to the wavelength exhibiting the maximum intensity. Net radiant powers exposed to the fluid ranged from about 1.7 J cm$^{-2}$ to about 3.5 J cm$^{-2}$. The surface area of the containers that receives electromagnetic radiation from the electromagnetic radiation sources positioned above and below the containers is about 584 cm$^2$. The containers employed in these experiments have a 110 cm$^2$ area corresponding to a label which does not transmit electromagnetic radiation from the electromagnetic radiation sources. The surface area value of 584 cm$^2$, referenced above, takes into consideration (i.e. does not include) the presence of the 110 cm$^2$ nontransmissive label.

In the present example, two types of illumination conditions were employed and compared to each other. In one series of experiments, platelet and plasma-containing samples were exposed to a constant net radiant energy equal to about 3 J cm$^{-2}$, regardless of the volume of each fluid sample In a second series of experiments, platelet and plasma-containing samples were exposed to net radiant energies determined using the following equation:

$$E_{net} = \left(6.24 \ \frac{J}{cm^3}\right) \times \left(\frac{V(cm^3)}{(584 \ cm^2)}\right); \quad (V)$$

wherein $E_{net}$ is net radiant energy in units of joules per square centimeter, V is volume of the fluid sample and 584 cm$^2$ is the surface area of the container which receives electromagnetic radiation from the two electromagnetic radiation sources.

Platelet and plasma-containing fluids were continuously mixed during illumination by providing a substantially constant container agitation rate of 120 agitation cycles per minute. In another set of experiments two container agitation rates were used corresponding to 120 cycles min.$^{-1}$ and 20 cycles min.$^{-1}$. Fluid samples were cooled during illumination by forced convection cooling such that they never exceeded a temperature of about 33° C.

Bovine viral diarrhea virus (BVDV), porcine parvovirus virus (PPV), hepatitis A virus (HAV) and *S. aureus* bacteria were assayed before and after illumination using TCID$_{50}$ or plating methods to provide quantitative measurements of the extent of pathogen reduction achieved. In addition, a number of cell quality indicators were measured to assess the quality of the treated blood components after treatment. As used herein, "cell quality indicator" refers to an indicator of cellular blood component quality. Exemplary cell quality indicators are parameters corresponding to the physical state of a fluid containing cells or cellular blood components that provide a measurement useful for assessing its quality for subsequent use in therapeutic applications.

Figure 4A:
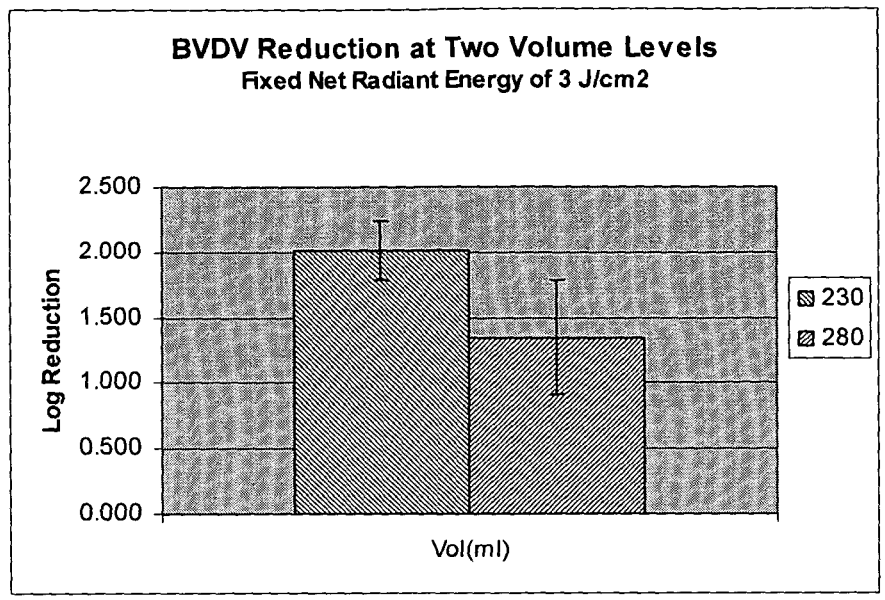
FIG. 4A provides a bar graph showing the average reduction of BVDV pathogen for fluid samples having two different volumes held in containers having nontransmissive labels and exposed to a fixed net radiant energy equal to 3 Joules $cm^{-2}$.
Figure 4B:
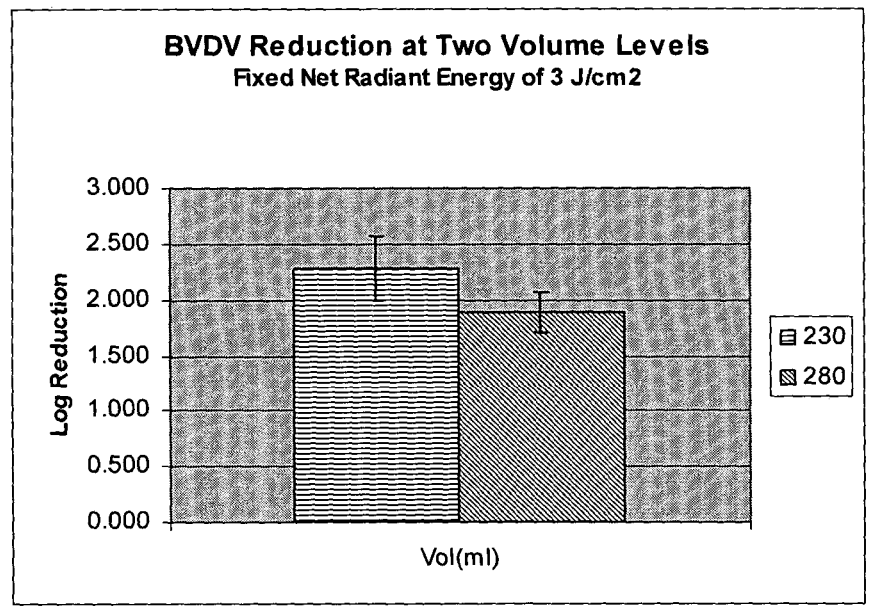
FIG. 4B provides a bar graph showing the average reduction of BVDV pathogen for fluid samples having two different volumes held in containers not having nontransmissive labels and exposed to a fixed net radiant energy equal to 3 Joules $cm^{-2}$. The error bars shown in FIGS. 4A and 4B correspond to standard deviations ($1\sigma$) corresponding to six independent measurements at each volume.

FIG. 4A provides a bar graph showing the average reduction of BVDV pathogen for fluid samples having two different volumes held in containers having nontransmissive labels and exposed to a fixed net radiant energy. Specifically, the net radiant energy provided to the fluid samples was equal to 3 Joules cm$^{-2}$ (i.e. 3 Joules per surface area of the container that receives electromagnetic radiation from the electromagnetic radiation sources), regardless of the volume of the samples. As shown in FIG. 4A, the extent of reduction in BVDV pathogen decreases from about 2.0 log to about 1.4 log upon increasing the volume of the fluid sample from about 230 ml to about 280 ml. The data in FIG. 4A was analyzed statistically via student's T test, which revealed that the observed difference in pathogen reduction for 230 mL and 280 mL samples is statistically significant (P value=0.004). Similar experiments were carried out using containers having different surface areas that transmit electromagnetic radiation from the electromagnetic radiation sources. These containers do not have nontransmissive labels, and thus have larger surface areas that transmit electromagnetic radiation from the electromagnetic radiation sources. FIG. 4B provides a bar graph showing the average reduction of BVDV pathogen for fluid samples having two different volumes held in containers not having nontransmissive labels and exposed to a fixed net radiant energy equal to 3 Joules cm$^{-2}$. As shown in FIG. 4B, the extent of reduction in BVDV pathogen decreases from about 2.3 log to about 1.9 log upon increasing the volume of the fluid sample from about 230 ml to about 280 ml. The data in FIG. 4B was analyzed statistically via student's T test, which revealed that the observed difference in pathogen reduction for 230 mL and 280 mL samples is statistically significant (P value=0.008). The data in FIGS. 4A and 4B illustrate that platelet and plasma-containing fluids having larger volumes undergo a statistically significantly smaller reduction in BVDV pathogen than platelet and plasma-containing fluids having smaller volumes when illuminated with equivalent net radiant energies. The error bars shown in FIGS. 4A and 4B correspond to standard deviations (1σ) corresponding to six independent measurements at each volume.

Figure 5:
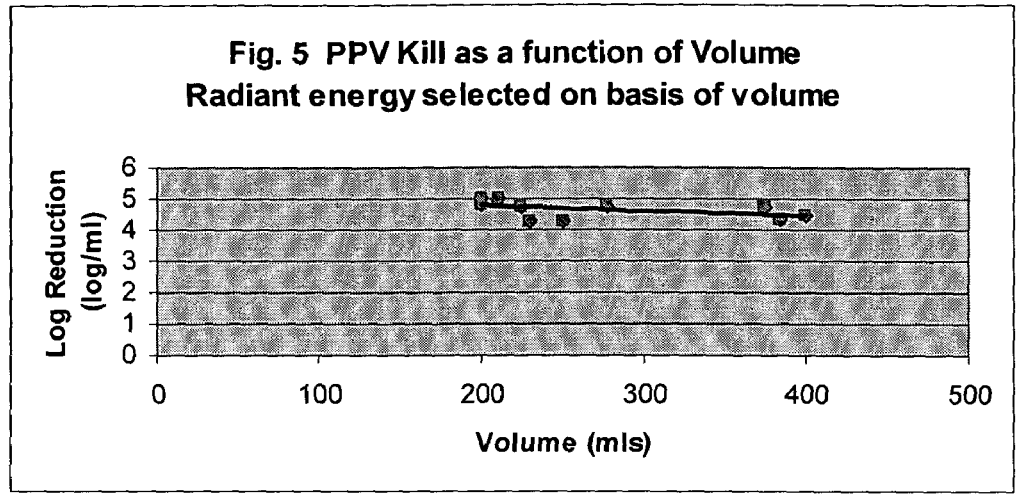
FIG. 5 shows the average reduction of porcine parvovirus virus (PPV) pathogen in human platelet and plasma-containing samples as a function of volume for fluid samples exposed to a net radiant energy which is calculated on the basis of volume.
Figure 6:
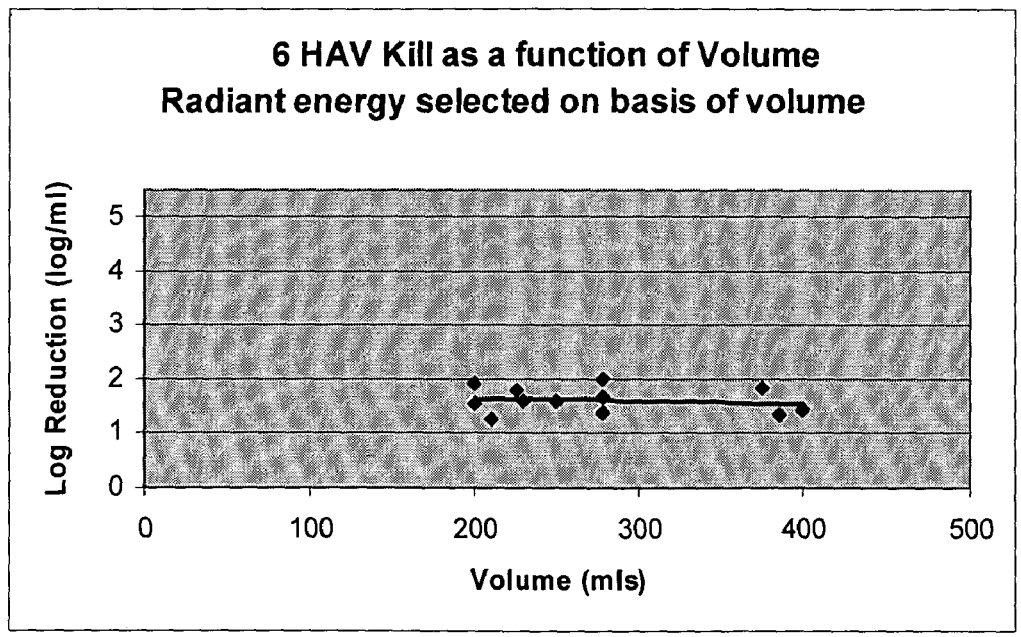
FIG. 6 shows the average reduction of hepatitis A virus (HAV) pathogen in human platelet and plasma-containing samples as a function of volume for fluid samples exposed to a net radiant energy which is calculated on the basis of volume.
Figure 7:
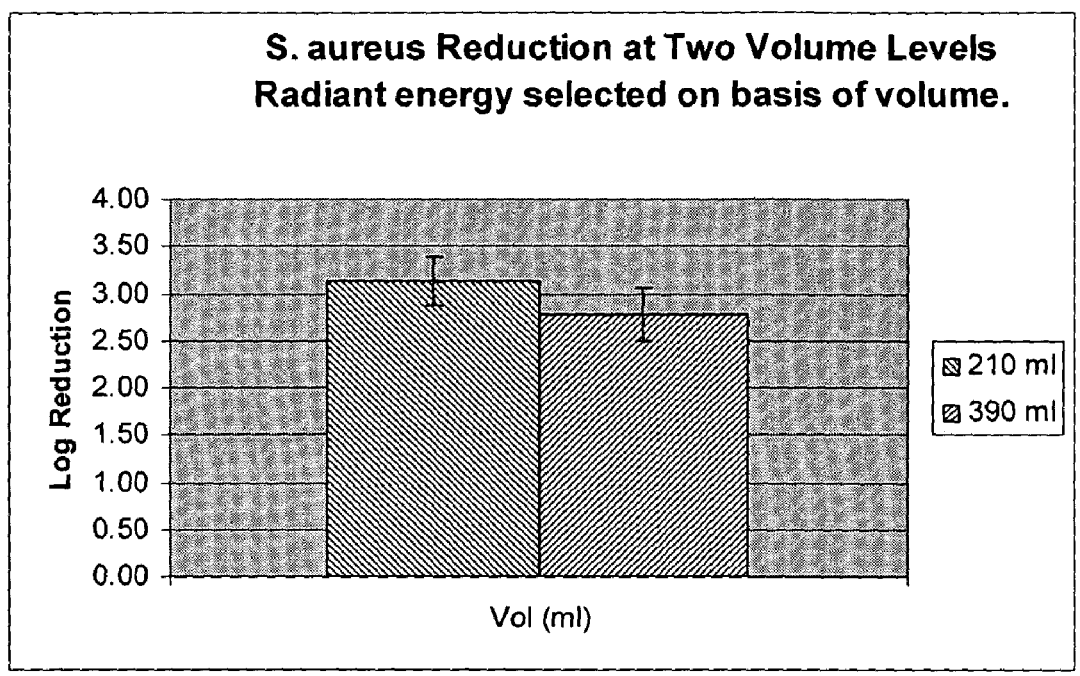
FIG. 7 provides a bar graph showing the average reduction of *S. aureus* bacteria for fluid samples having volumes of 210 mL and 390 mL exposed to net radiant energies calculated on the basis of volume using Equation V. The error bars shown in FIG. 7 correspond to time the standard deviation ($1\sigma$) corresponding to four independent measurements at each volume.

FIG. 5 shows the average reduction of PPV pathogen plotted as a function of volume for platelet and plasma-containing fluids exposed to net radiant energies calculated on the basis of volume using Equation V. FIG. 6 shows the average reduction of HAV pathogen plotted as a function of volume for platelet and plasma-containing fluids exposed to net radiant energies calculated on the basis of volume using Equation V. The plots in FIGS. 5 and 6 are essentially flat lines having a slope which includes zero within the uncertainties of their respective linear least square fits. FIG. 7 provides a bar graph showing the average reduction of S. aureus bacteria for fluid samples having volumes of 210 mL and 390 mL and exposed to net radiant energies calculated on the basis of volume using Equation V. The error bars shown in FIG. 7 correspond to time the standard deviation (1σ) corresponding to four independent measurements at each volume. The data in FIG. 7 was analyzed statistically via student's T test, which revealed that the observed difference in pathogen reduction for 210 mL and 390 mL samples is statistically insignificant (P value=0.06). A comparison of the graphs in FIGS. 4A and 4B with the plots and graphs in FIGS. 5, 6 and 7 illustrate that the use of net radiant energies derived from fluid volume provides uniform pathogen reduction regardless of sample volume.

The extent of pathogen reduction achieved using net radiant energies determined by Equation V was also measured for a range of platelet concentrations. These experiments showed that the extent of pathogen reduction achieved using net radiant energies derived from sample volume was independent of platelet concentration over a range of platelet concentrations ranging from about 1000×10³ platelets per microliter to about 2000×10³ platelets per microliter.

The rate of glucose consumption, the rate of lactate production and pH was determined to assess the quality of treated fluid samples treated with electromagnetic radiation. During metabolism, cells consume glucose and generate two lactate molecules for each glucose molecule consumed. The lactate formed has the effect of lowering the pH of the blood component sample. As a finite amount of glucose is provided to cells during storage, stored cellular blood components which consume glucose too quickly are degraded. Lower glucose consumption rates and lactate production rates are indicative of cellular blood components that retain a high therapeutic effectiveness when stored. Therefore, low glucose consumption rates and lactate production rates are considered indicator of high cell quality.

Table I shows the pH, rate of glucose consumption and rate of lactate production for platelet and plasma-containing samples having volumes of 200 ml and 250 ml that are exposed to a fixed net radiant energy of 3 J cm⁻². As shown in Table I, 250 mls plasma and platelet-containing samples exhibit significantly lower rates of glucose consumption and rates of lactate production than 200 ml plasma and platelet-containing samples. Table II shows the pH, rate of glucose consumption and rate of lactate generation for platelet and plasma-containing samples having volumes between 200 and 225 ml and platelet and plasma-containing samples having volumes between 375 and 400 ml that are exposed to net radiant energies determined using Equation V. In contrast to the data in Table I, no trend in the rate of glucose consumption and the rate of lactate generation can be discerned with respect to sample volume in the data in Table II. Specifically, all the samples investigated have glucose consumption rates and lactate production rates that are within the uncertainties of these measurements regardless of their sample volumes. Moreover, the glucose consumption rate and lactate production rate data shown in Table II reflect a change in volume approximately two times greater than the data shown in table I. In combination, the data in Tables I and II demonstrate that use of net radiant energies based on volume provides treated blood components which exhibit substantially uniform cell quality indicators regardless of sample volume.

TABLE I

Cell Quality Results for Platelet and Plasma-containing Samples Treated with a Fixed Net Radiant Energy of 3 J cm⁻².

| CQ Parameter | Volume = 200 mL | Volume = 250 mL |
|---|---|---|
| pH (22° C.) | 6.95 ± 0.02 | 7.03 ± 0.08 |
| Lactate Rate (mmol/10¹² cells/hr) | 0.086 ± 0.009 | 0.061 ± 0.009 |
| Glucose Rate (mmol/10¹² cells/hr) | 0.048 ± 0.014 | 0.033 ± 0.005 |
| P-selectin (%) | 70.1 ± 14.6 | 52.7 ± 21.3 |

TABLE II

Cell Quality Results for Platelet and Plasma-containing Samples Treated with Radiant Energies Calculated on the Basis on Sample Volume.

| CQ Parameter | Volume = 200 to 225 mL | Volume = 375 to 400 mL |
|---|---|---|
| pH (22° C.) | 7.19 ± 0.13 | 7.12 ± 0.19 |
| Lactate Rate (mmol/10¹² cells/hr) | 0.085 ± 0.017 | 0.070 ± 0.019 |
| Glucose Rate (mmol/10¹² cells/hr) | 0.044 ± 0.011 | 0.040 ± 0.010 |
| P-selectin (%) | 48.4 ± 14.8 | 47.5 ± 13.1 |

Premature activation of platelets during storage may degrade their ability to be subsequently used in therapeutic procedures. P-selectin, also known as GMP-140, is a protein expressed when cells are activated and, thus, provides a quantitative measure of the ability of platelet containing samples to survive long term storage conditions. It has been previously demonstrated that low p-selectin levels in platelet-containing samples are indicative of good storage and subsequent therapeutic qualities [Transfusion, Vol 42, pgs. 847-854 (2002) and Transfusion Vol 42 pgs. 1333-1339 (2002)]. To assess the quality of platelet and plasma containing samples treated by the present methods, the percentage of cells expressing p-selectin was measured after treatment of a fluid sample with electromagnetic radiation.

Table I shows the percentage of cells expressing p-selectin for 200 ml samples and 250 ml samples that are exposed to a fixed net radiant energy of 3 J cm⁻³. As shown in Table I, 250 ml samples exhibit a significantly lower percentage of cells expressing p-selectin than 200 ml samples for illumination with a fixed net radiant energy. Table II shows the percentage of cells expressing p-selectin for samples that are exposed to a net radiant energies calculated using Equation V having volumes from 200 ml to 225 ml and having volumes from 375 ml to 400 ml. As shown in Table II, samples having volumes from 200 ml to 225 ml and samples having volumes from 375 ml to 400 ml exhibit substantially identical percentages of cells expressing p-selectin. Moreover, the percentage p-selectin data shown in Table II reflect a change in volume approximately two times greater than the data shown in table I. A comparison of the Data in Tables I and II, demonstrate that treatment of platelet containing samples with radiant energies derived from sample volume provides cellular blood compounds that exhibit uniform cellular quality indicators which do not vary significantly with sample volume.

Uniformity of the protein composition of plasma containing samples treated by the methods of the present invention was also quantitatively verified. In these studies, 200 mL and 400 mL samples were treated with net radiant energies determined using Equation V and subsequently evaluated with respect to the concentrations of a number of plasma proteins in the treated samples. Table III shows the average concentrations of proteins assayed in six treated 200 mL samples and six treated 400 mL samples and values corresponding to the highest and lowest measurements in sets of six measurements corresponding to each volume. A comparison of the protein concentrations in Table III shows that the concentrations of assayed proteins for treated 200 mL and 400 mL plasma containing samples were in many cases identical and always within their respective high and low ranges. These results indicate that the present methods are capable of uniformly treating plasma-containing fluids with electromagnetic radiation, and that samples treated by the present methods have compositions that do not vary significantly as a function of volume

TABLE III

Protein Concentrations for Plasma-containing Samples Treated with Radiant Energies Calculated on the Basis on Sample Volume

| Assay | 200 mL Plasma Mean (Min.-Max.) (N = 6) | 400 mL Plasma Mean (Min.-Max.) (N = 6) |
|---|---|---|
| Fibrinogen (mg/dL) | 234 (162-276) | 241 (179-282) |
| Factor II (I.U./mL) | 0.79 (0.65-0.89) | 0.80 (0.66-0.92) |
| Factor VII (I.U./mL) | 0.85 (0.62-1.08) | 0.85 (0.62-1.09) |
| Factor IX (I.U./mL) | 0.84 (0.51-1.04) | 0.85 (0.57-1.04) |
| Factor X (I.U./mL) | 0.89 (0.64-1.02) | 0.90 (0.67-1.03) |
| Factor XI (I.U./mL) | 0.74 (0.60-0.87) | 0.74 (0.59-0.89) |
| Factor XII (I.U./mL) | 0.79 (0.41-1.13) | 0.81 (0.41-1.20) |
| Prekallikrein (I.U./mL) | 0.65 (0.54-0.79) | 0.71 (0.66-0.79) |
| High MW Kininogen (I.U./mL) | 0.84 (0.68-1.00) | 0.85 (0.70-0.98) |
| Factor XIIa (ng/mL) | 3.6 (1.8-4.9) | 3.8 (2.2-4.8) |
| Antithrombin (I.U./mL) | 0.92 (0.86-1.07) | 0.94 (0.82-1.13) |
| Protein C (I.U./mL) | 0.87 (0.69-1.06) | 0.85 (0.66-1.07) |
| Protein S (I.U./mL) | 0.98 (0.80-1.20) | 0.84 (0.72-1.04) |

The effect of agitation rate on the extent of pathogen reduction achieved upon treatment of fluids with electromagnetic radiation was also studied by varying the agitation rate provided to the sample container during illumination. Platelet and plasma-containing samples were exposed to net radiant energies calculated using Equation V. Samples were mixed during illumination using two different agitation rates: 120 cycles per minute and 20 cycles per minute. Platelet and plasma containing samples mixed using an agitation rate of 120 cycles per minute exhibited a 4.65 log decrease in the biological activity of PPV pathogens and platelet and plasma containing samples mixed using an agitation rate of 20 cycles per minute exhibited a 0.72 log decrease in the biological activity of PPV pathogens. These results demonstrate that to provide effective pathogen reduction throughout a fluid sample the rate of fluid mixing during illumination must be sufficiently large to efficiently transport photosensitizers into and out of the photoreactive layer. Particularly, the time scale in which the fluid is mixed must be matched to the time scale in which radiant energy is introduced to a sample to optimize pathogen reduction.

We claim:

1. A method for reducing pathogens in a fluid, said method comprising the steps of:
    providing the fluid held in an at least partially transparent container,
    wherein the fluid comprises particles;
    determining the volume of the fluid;
    mixing the fluid held in the at least partially transparent container;
    calculating a net radiant energy for reducing said pathogens in the fluid using the volume determined for the fluid and the mixing rate of the fluid wherein the net radiant energy is substantially linearly related to the volume and substantially inversely linearly related to said mixing rate; and
    providing electromagnetic radiation having said net radiant energy to the fluid, thereby generating a photoreactive layer positioned adjacent to an illuminated surface of the fluid wherein said electromagnetic radiation interacts with said particles and wherein said electromagnetic radiation has an intensity sufficient to initiate chemical or physical changes in the fluid;
    and wherein mixing the fluid in said container transports the particles through the photoreactive layer, thereby reducing pathogens in the fluid.

2. The method of claim 1 wherein the calculated net radiant energy with respect to the volume is determined using the expression:

$$E_{net} = Z \times \frac{(V)}{(A)} + b;$$

wherein $E_{net}$ is the calculated net radiant energy, V is the volume of the fluid, Z is a first constant having a value greater than zero, b is a second constant and A is the surface area of the container that transmits the electromagnetic radiation to the fluid.

3. The method of claim 2 wherein the volume of the fluid is a value selected from the range of values of about 200 ml to about 400 ml and wherein said first constant (Z) is equal to about 6.24 J cm$^{-3}$, and said second constant (b) has a value equal to about 0.

4. The method of claim 1 wherein said step of determining the volume of the fluid comprises the steps of:
    measuring the mass of the fluid; and
    dividing said mass of the fluid by the density of the fluid, thereby determining the volume of the fluid.

5. The method of claim 1 wherein said step of mixing the fluid held in the at least partially transparent container transports the entire volume of the fluid through said photoreactive layer, thereby reducing pathogens throughout the entire volume of the fluid.

6. The method of claim 1 further comprising the step of adding a photosensitizer to the fluid, and wherein said step of determining the volume of the fluid comprises determining the volume of the fluid having said photosensitizer.

7. The method of claim 6 wherein said photosensitizer is 7,8-dimethyl-10-ribityl isoalloxazine.

8. The method of claim 1 wherein substantially all of said particles are exposed to equivalent effective net radiant energies.

9. The method of claim 1 wherein the fluid is a biological fluid.

10. The method of claim 9 wherein said biological fluid is selected from the group consisting of:
   whole blood;
   a blood component;
   a red blood cell-containing blood component;
   a plasma-containing blood component;
   a platelet-containing blood component;
   a white blood cell-containing blood component;
   a solution containing one or more proteins derived from blood; and
   a peritoneal solution, and
   wherein said method further comprises setting the net radiant energy based on the composition of the fluid including the concentration and identity of the components comprising the biological fluid.

11. The method of claim 1 wherein said electromagnetic radiation provided to the fluid has wavelengths in the ultraviolet region of the electromagnetic spectrum.

12. The method of claim 1 wherein said electromagnetic radiation provided to the fluid has wavelengths in the visible region of the electromagnetic spectrum.

13. The method of claim 1 wherein said step of mixing the fluid held in the at least partially transparent container comprises agitating the fluid held in the at least partially transparent container.

14. The method of claim 1 wherein the electromagnetic radiation having said net radiant energy is provided to the fluid by providing a selected radiant power for a selected illumination period.

15. A method for reducing pathogens in a fluid, said method comprising the steps of:
   providing the fluid held in an at least partially transparent container,
   wherein the fluid comprises particles;
   mixing the fluid held in the at least partially transparent container at a selected mixing rate;
   calculating a net radiant energy for reducing said pathogens in the fluid using the selected mixing rate of the fluid, wherein said net radiant energy is substantially inversely linearly related to said mixing rate; and
   providing electromagnetic radiation having said net radiant energy to the fluid, thereby generating a photoreactive layer positioned adjacent to an illuminated surface of the fluid wherein said electromagnetic radiation interacts with said particles and wherein said electromagnetic radiation has an intensity sufficient to initiate chemical or physical changes in the fluid;
   and wherein mixing the fluid in said container transports said particles through said photoreactive layer, thereby reducing pathogens in the fluid.

16. The method of claim 15 wherein substantially all of said particles are exposed to equivalent effective net radiant energies.

17. The method of claim 15 wherein said step of mixing the fluid held in the at least partially transparent container at a selected mixing rate comprises agitating the fluid held in the at least partially transparent container.

18. The method of claim 15 wherein said step of mixing the fluid held in the at least partially transparent container transports the entire volume of the fluid through said photoreactive layer, thereby reducing pathogens throughout the entire volume of the fluid.

19. The method of claim 15 further comprising the step of adding a photosensitizer to the fluid.

20. The method of claim 15 wherein said photosensitizer is 7,8-dimethyl-10-ribityl isoalloxazine.

21. A method for uniformly treating a plurality of fluid samples with electromagnetic radiation, said method comprising the steps of:
   providing said plurality of fluid samples, wherein each fluid sample comprises particles;
   providing each of the fluid samples held in at least partially transparent containers;
   determining the volumes of each of the fluid samples held in at least partially transparent containers;
   mixing each of the fluid samples held in the at least partially transparent containers;
   calculating net radiant energies for each of the fluid samples using the volumes determined for each of the fluid samples and the mixing rate,
   wherein the net radiant energies are directly related to the volume and inversely related to the mixing rate;
   providing electromagnetic radiation having said net radiant energies to each of the fluid samples, thereby generating photoreactive layers in each of the fluid samples positioned adjacent to an illuminated surface of each of the fluid samples, wherein said electromagnetic radiation interacts with said particles in photoreactive layers of each fluid sample and wherein said electromagnetic radiation in said photoreactive layers of each fluid sample has intensities sufficient to initiate chemical or physical changes in the fluid samples; and wherein mixing the fluid samples transports said particles through said photoreactive layers, thereby uniformly treating the plurality of fluid samples with electromagnetic radiation.

22. The method of claim 21 wherein the calculated net radiant energies provided to each of the fluid samples are related to the volumes of each of the fluid samples in a substantially linear manner.

23. The method of claim 21 wherein said step of mixing each of the fluid sample held in at least partially transparent containers transports the entire volumes of the fluid samples through said photoreactive layers, thereby reducing pathogens throughout the entire volumes of the fluid samples.

24. The method of claim 21 wherein the calculated net radiant energies provided to each fluid sample are provided by the expression:

$$E_{net} = Z \times \frac{(V)}{(A)} + b;$$

wherein $E_{net}$ is the net radiant energy, V is said volume of the fluid sample, Z is a first constant having a value greater than zero, b is a second constant and A is the surface area of the container that transmits the electromagnetic radiation provided to the fluid sample.

25. The method of claim 24 wherein the volumes of the fluid samples are selected from the range of values of about 200 ml to about 400 ml and wherein said first constant (Z) is equal to about 6.24 J cm$^{-3}$, and said second constant (b) has a value equal to about 0.

26. The method of claim 21 wherein substantially all of said particles comprising all of the fluid samples are exposed to equivalent effective net radiant energies.

27. The method of claim 21 wherein said step of determining the volumes of each of the fluid samples comprises the steps of:
measuring the masses of each of the fluid samples; and
dividing the masses of each of the fluid samples by estimates of the densities of each of the fluid samples, thereby determining the volumes of each of the fluid samples.

28. The method of claim 21 wherein said step of mixing each of the fluid samples comprises agitating each of the fluid samples held in at least partially transparent containers.

29. A method for uniformly treating a plurality of fluid samples with electromagnetic radiation, said method comprising the steps of:
providing said plurality of fluid samples, wherein each fluid sample comprises particles;
providing each of the fluid samples held in at least partially transparent containers;
mixing each of the fluid samples held in at least partially transparent containers at selected fluid mixing rates;
calculating net radiant energies for each of the fluid samples using the selected fluid mixing rates for each of the fluid samples, wherein the net radiant energies are inversely related to the mixing rate;
providing electromagnetic radiation having said net radiant energies to each of the fluid samples, thereby generating photoreactive layers in each of the fluid samples positioned adjacent to an illuminated surface of each of the fluid samples, wherein said electromagnetic radiation interacts with said particles in photoreactive layers of the fluid samples and wherein said electromagnetic radiation in said photoreactive layers of each fluid sample has intensities sufficient to initiate chemical or physical changes in the fluid samples; and wherein mixing the fluid samples transports said particles through said photoreactive layers, thereby uniformly treating the plurality of fluid samples with electromagnetic radiation.

30. The method of claim 29 wherein substantially all of said particles comprising all of the fluid samples are exposed to equivalent effective net radiant energies.

31. The method of claim 29 wherein said step of mixing each fluid sample held in at least partially transparent containers transports the entire volumes of the fluid samples through said photoreactive layers, thereby reducing pathogens throughout the entire volumes of the fluid samples.

32. The method of claim 29 wherein said step of mixing each of the fluid samples held in at least partially transparent containers at selected fluid mixing rates comprises agitating each of the fluid samples held in at least partially transparent containers.

33. A system for reducing pathogens in a volume of a fluid comprising particles, said system comprising:
a partially transparent container for holding the fluid;
a means for mixing the fluid at a selected mixing rate;
a light source controller for determining a net radiant energy for reducing pathogens in the fluid, wherein said light source controller calculates said net radiant energy based on the volume of the fluid and the selected mixing rate, wherein the net radiant energy is inversely related to the mixing rate of the fluid by operation of the algorithm and wherein said light source controller generates an output signal corresponding to said calculated net radiant energy; and
a source of electromagnetic radiation operationally connected to said light source controller for receiving the output signal corresponding to said calculated net radiant energy, and for exposing the fluid to electromagnetic radiation having said net radiant energy thereby generating a photoreactive layer positioned adjacent to an illuminated surface of the fluid wherein said electromagnetic radiation interacts with said particles and wherein said electromagnetic radiation has an intensity sufficient to initiate chemical or physical changes in the fluid;
whereby mixing of the fluid circulates said particles through the photoreactive layer, thereby reducing pathogens in the volume of the fluid.

34. The system of claim 33 wherein the light source controller executes an algorithm that determines the net radiant energy, and wherein the net radiant energy is substantially linearly related to the volume of the fluid by operation of the algorithm.

35. The system of claim 34 wherein said algorithm determines the net radiant energy with respect to the volume using the expression:

$$E_{net} = Z \times \frac{(V)}{(A)} + b;$$

wherein $E_{net}$ is the net radiant energy, V is said volume of the fluid, Z is a first constant having a value greater than zero, b is a second constant and A is the surface area of the container that transmits the electromagnetic radiation provided to the fluid sample.

36. The method of claim 35 wherein the volume of the fluid is a value selected from the range of values of about 200 ml to about 400 ml and wherein said first constant (Z) is equal to about 6.24 J cm$^{-3}$, and said second constant (b) has a value equal to about 0.

37. The system of claim 33 further comprising a means of determining the volume of the fluid.

38. The system of claim 33 wherein the means for mixing the fluid at a selected mixing rate is an agitator operationally connected to said partially transparent container.

39. The system of claim 33 wherein mixing the fluid held in the at least partially transparent container transports the entire volume of the fluid through said photoreactive layer, thereby reducing pathogens throughout the entire volume of the fluid.

40. The system of claim 33 wherein substantially all of said particles comprising the fluid are exposed to equivalent effective net radiant energies.

41. The system of claim 33 wherein said source of electromagnetic radiation provides electromagnetic radiation having wavelengths in the ultraviolet region of the electromagnetic spectrum, visible region of the electromagnetic spectrum or both to the fluid.

* * * * *